United States Patent [19]
Knoff et al.

[11] Patent Number: 5,325,301
[45] Date of Patent: Jun. 28, 1994

[54] METHOD OF ANALYZING THE TEXTURE OF A SURFACE AND A CARPET CHARACTERIZED BY THE METHOD

[75] Inventors: Warren F. Knoff, Richmond, Va.; Michael J. Merrill, New Castle, Del.; Barry Rubin, Glen Mills, Pa.; Akhileswar G. Vaidyanathan, Hockessin, Del.; James E. Van Trump; Theresa A. Weston, both of Wilmington, Del.

[73] Assignee: E. I. Du Pont de Nemours and Company, Wilmington, Del.

[21] Appl. No.: 860,774

[22] Filed: Mar. 27, 1992

Related U.S. Application Data

[63] Continuation-in-part of Ser. No. 733,353, Jul. 17, 1991, abandoned.

[51] Int. Cl.$^5$ .............................................. G06F 15/20
[52] U.S. Cl. ...................................... 364/552; 428/89
[58] Field of Search ............... 250/550, 559, 562, 563, 250/565, 208.1, 227.16, 227.17, 227.2, 574; 364/552, 470; 428/89

[56] References Cited

U.S. PATENT DOCUMENTS

| | | | |
|---|---|---|---|
| 3,044,145 | 7/1962 | Tager et al. | 28/1 |
| 3,816,583 | 6/1974 | Kashima et al. | 264/282 |
| 4,051,722 | 10/1977 | Feller | 364/552 |
| 4,103,177 | 7/1978 | Sanford et al. | 250/562 |
| 4,839,211 | 6/1989 | Wilkie et al. | 428/89 |
| 5,058,371 | 10/1991 | Yu et al. | 57/239 |
| 5,146,550 | 9/1992 | Furter et al. | 364/552 |

FOREIGN PATENT DOCUMENTS

| | | |
|---|---|---|
| 45-3001 | 4/1965 | Japan . |
| 45003001 | 4/1965 | Japan . |

OTHER PUBLICATIONS

Haralick, Shanmugan and Dinstein, "Textural Features For Image Classification," IEEE Transactions on Systems, Man and Cybernetics, vol. SMC-3, No. 6, Nov. 1973, pp. 610-621.

Siew, Hodgson and Wood, "Texture Measures for Carpet Wear Assessment," IEEE Transactions on Pattern Analysis and Machine Intelligence, vol. 10, No. 1, Jan. 1988, pp. 92-105.

Wu, University of Maryland, "New Imaging Techniques for Quantifying Carpet Appearance," Textile Chemist and Colorist, vol. 23, No. 4, Apr., 1991, pp. 25-29.

Sobus, Pourdeyhimi, Gerde and Ulcay, "Assessing Changes in Texture Periodicity Due to Appearance Loss in Carpets: Grey Level Co-Occurrence Analysis," Textile Research Journal, vol. 61, No. 10, Oct. 1991, pp. 557-567.

*Primary Examiner*—Jack B. Harvey
*Assistant Examiner*—Thomas Peeso
*Attorney, Agent, or Firm*—Jane E. Obee

[57] ABSTRACT

The present invention relates broadly to a method of image analysis for analyzing the texture of a surface, and to a saxony-type carpet having a tightly tailored surface texture characterized by this method. The method employs a model based on a second order co-occurrence matrix model which calculates a set of textural parameters for image classification. This co-occurrence matrix model examines the statistics of the spatial relationship between gray levels in a homogeneously textured image with calculated textural features which represent measures such as homogeneity and contrast. The method of the present invention uses this model to construct a set of normalized textural parameters from the textural parameters and calculates a value for the normalized textural parameters from this set, where the normalized textural parameters are related to the physical properties of the surface, such as pile lay of a carpet. The method compares the value for each of the normalized textural parameters of an unknown sample to the value for each of the corresponding normalized textural parameters for a known, or goal, sample. In one embodiment, the method compares an unknown sample of a saxony-type carpet to a goal sample of a saxony-type carpet having a tightly tailored surface texture to determine whether the unknown sample is such a carpet.

26 Claims, 11 Drawing Sheets

FIG. 14

| SAMPLE | $C_1$ $D_2P_2$ | $C_2$ $D_2P_4$ | $C_3$ $D_2P_2$ | $C_4$ $D_4P_4$ | NDD | NSD | NS | VISUAL RATING | QUALITY |
|---|---|---|---|---|---|---|---|---|---|
| S1 | 2704.4 | 2927.4 | 2561.2 | 3029.2 | 22 | 25 | 252 | 1 | FAIL |
| S2 | 2681.1 | 1956.8 | 2257.8 | 2303.3 | 74 | 33 | 206 | 2 | FAIL |
| S3 | 1494.8 | 1607.1 | 1179.9 | 1918.4 | 101 | 55 | 139 | 3 | PASS |
| S4 | 990.9 | 1154.3 | 752.5 | 1563.3 | 145 | 87 | 100 | 4 | PASS |
| S5 | 987.8 | 960.2 | 745.1 | 1458.8 | 165 | 71 | 93 | 5 | FAIL |
| S6 | 594.4 | 1334.7 | 610.1 | 1832.5 | 110 | 180 | 98 | 6 | FAIL |
| SAX | 1659.9 | 533.0 | 1541.8 | 620.2 | 47 | 188 | 98 | OFF SCALE | FAIL |
| P00 | 2703.1 | 2116.1 | 2445.3 | 2226.4 | 39 | 34 | 213 | OFF SCALE | FAIL |
| U1 | 1987.0 | 1129.4 | 1325.2 | 1321.3 | 148 | 60 | 129 | 5 | FAIL |
| U2 | 1948.2 | 1038.0 | 1181.7 | 1240.3 | 157 | 72 | 121 | 5 | FAIL |
| U3 | 1818.2 | 1036.2 | 1088.4 | 1404.2 | 87 | 82 | 120 | 3.5 | PASS |
| U4 | 1493.3 | 848.4 | 967.5 | 1062.0 | 126 | 68 | 98 | 3.5 | PASS |
| U5 | 1903.9 | 972.0 | 1081.4 | 1293.4 | 137 | 87 | 118 | 3.5 | PASS |
| U6 | 1695.0 | 962.0 | 993.7 | 1323.6 | 81 | 84 | 112 | 3.5 | PASS |
| U7 | 1811.0 | 878.6 | 1151.1 | 1113.5 | 181 | 78 | 111 | 5.5 | FAIL |
| U8 | 2008.7 | 2168.7 | 1897.1 | 2925.3 | 96 | 53 | 202 | OFF SCALE | FAIL |
| U9 | 1780.6 | 881.3 | 1012.2 | 1023.6 | 189 | 78 | 105 | 4 | PASS |
| U10 | 1571.2 | 1548.4 | 1381.7 | 1839.9 | 69 | 30 | 142 | 1.5 | FAIL |
| U11 | 1448.4 | 625.1 | 962.3 | 968.8 | 204 | 83 | 90 | 4.5 | FAIL |

FIG. 13

| SAMPLE | F-STOP SETTING | $C_1$ $D_2P_2$ | $C_2$ $D_2P_4$ | $C_3$ $D_2P_2$ | $C_4$ $D_4P_4$ | NDD | NSD |
|---|---|---|---|---|---|---|---|
| S3 | 5.6 | 1820.1 | 1736.1 | 1354.6 | 2211.7 | 109 | 53 |
| S3 | 8 | 554.2 | 567.5 | 426.7 | 719.6 | 123 | 54 |
| SAX | 5.6 | 1833.9 | 612.2 | 1714.7 | 721.6 | 47 | 181 |
| SAX | 8 | 634.7 | 190.2 | 559.7 | 218.6 | 64 | 196 |

FIG. 15

| SAMPLE | $C_1$ $D_2P_2$ | $C_2$ $D_2P_4$ | $C_3$ $D_2P_2$ | $C_4$ $D_4P_4$ | NSD |
|---|---|---|---|---|---|
| SAX$_1$ | 1743.5 | 557.5 | 1579.3 | 619.4 | 191 |
| SAX$_2$ | 1728.9 | 546.1 | 1567.5 | 615.2 | 192 |
| SAX$_3$ | 1740.6 | 547.0 | 1634.9 | 596.5 | 198 |
| SAX$_4$ | 1723.5 | 539.7 | 1606.8 | 607.3 | 195 |

METHOD OF ANALYZING THE TEXTURE OF A SURFACE AND A CARPET CHARACTERIZED BY THE METHOD

This application is a continuation-in-part of application Ser. No. 07/733,353, filed Jul. 17, 1991, now abandoned.

MICROFICHE APPENDIX

Attached hereto is a microfiche appendix containing 25 frames of modules which can be employed in the described embodiments. This microfiche appendix is included as a portion of the disclosure of this patent document.

COPYRIGHT NOTICE

A portion of the disclosure of this patent document contains material which is subject to copyright protection. The copyright owner has no objection to the reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

The present invention relates to an image processing method for analyzing the texture of a surface and a carpet characterized by this method.

2. Description of the Related Art

Traditionally, carpet texture has been characterized by a subjective technique which uses the assessment of panels of expert judges. Such a technique suffers from obvious deficiencies in consistency, including the lack of consistency over time and among differing panel members. Moreover, such a technique lacks an independent method of absolute quantification.

The present invention proposes the use of image processing techniques for the analysis of carpet texture. The image analysis model used in the present invention is based on the second order co-occurrence matrix model originally proposed by Haralick, Shanmugan and Dinstein in an article entitled "Textural Features for Image Classification," IEEE Transactions on Systems, Man and Cybernetics, Vol. SMC-3, No. 6, November 1973, pp. 610-621. This model, known as the Haralick model, examines the statistics of the spatial relationship between gray levels in a homogeneously textured image and calculates a set of textural features which quantify measures such as homogeneity and contrast. The Haralick model has been applied to carpet wear assessment by Siew, Hodgson and Wood as published in an article entitled "Texture Measures for Carpet Wear Assessment," IEEE Transactions on Pattern Analysis and Machine Intelligence, Vol. 10, No. 1, January 1988, pp. 92-105. This application of the Haralick model differs from the method of the present invention in that no attempt is made to construct a set of normalized textural parameters which are independent of any variations in the instruments used to generate an image of the carpet.

Papers describing image analysis techniques for carpet assessment have been published by the University of Maryland. In an article entitled "New Imaging Techniques for Quantifying Carpet Appearance," Textile Chemist and Colorist, Vol. 23, No. 4, April, 1991, pp. 25-29, Y. Wu of the University of Maryland characterizes the changes in textural appearance of carpet due to wear by carpet tuft size distribution and evenness of tuft spatial distribution. In contrast to the present invention, Wu's method is restricted to a localized analysis. In another article published by the University of Maryland entitled "Assessing Changes in Texture Periodicity Due To Appearance Loss in Carpets: Grey Level Co-Occurrence Analysis," Textile Research Journal, Vol. 61, No. 10, October, 1991, pp. 557-567, by J. Sobus, B. Pourdeyhimi, J. Gerde and Y. Ulcay, the Haralick co-occurrence matrix model was applied to characterizing carpet texture. This work differs from the present invention in that the image analyzed by this work is pre-processed using histogram equalization. Moreover, Sobus et al. do not further construct a set of normalized textural parameters which are linked to the physical properties of carpet and are independent of instrument variations.

The need exists for analyzing the surface texture of a saxony-type carpet, since a large portion of carpets used in residences are cut pile carpets which include saxony-type carpets. In saxony-type carpets, heat-set ply-twisted pile yarn is inserted into a backing material as loops which are then cut to form substantially parallel vertical tufts. The tufts are then evenly sheared to a desired height which is typically medium length. Generally, there are two different styles of saxony-type carpets: 1) a straight-set style in which the fibers at the tuft tip are straight and substantially perpendicular to the plane of the carpet face, and 2) a textured style in which the tufts and the individual fibers have varying degrees of curl.

Yarn which is used as pile in textured saxony-type carpets is prepared by cabling together two or more singles yarns, heat-setting them in their twisted condition, and finally drying them. One known method of processing the ply-twisted yarn prior to making the carpet involves feeding it through a stuffer box, where the yarn is axially compressed, and then passing it through a continuous heat-setting machine, known as a Superba ®, which treats the yarn with pressurized, saturated steam to heat-set the twist. Another known method involves feeding the ply-twisted yarn through the stuffer box, and then passing it through a continuous heat setting machine, known as a Suessen, which treats the yarn with dry heat to heat-set the twist.

Depending on the twist level of the yarns and other factors, such as the operating conditions of the stuffer box, textured saxony-type carpets may exhibit different surface textures or appearances. For example, a frieze carpet is made from pile yarns having a "high ply-twist". By the term "high ply-twist" as used herein, it is meant a ply-twist level greater than about 5.5 turns per inch (tpi) (2.17 turns per centimeter (tpc)). When highly-ply twist yarn is tufted into a carpet, the tufts demonstrate a highly-kinked and curled effect with gross buckling of the tuft structures. Such a carpet has a surface texture similar to the surface texture shown in FIG. 1. In other instances, a textured saxony-type carpet may have a loose surface texture with open tuft tips forming a brush-like appearance. Such a carpet has a surface texture similar to the surface shown in FIG. 6. This texture approaches the appearance of a straight-set, saxony-type carpet. These carpets are typically made from "low ply-twist" pile yarns. By the term "low ply-twist" as used herein, it is meant a ply-twist level less than about 4.25 turns per inch (1.67 turns per centimeter). Other textured saxony-type carpets are characterized by loose surface textures having open tuft tips, where many of the yarns have an unraveled structure.

Such a surface texture is even looser than the texture of the carpet as shown in FIG. 6. These carpets are typically made from "low ply-twist" pile yarns which have been treated by a process where steam is injected directly into the stuffer box.

A textured saxony-type carpet may also be referred to as a "trackless" carpet. Examples of trackless carpet are disclosed in U.S. Pat. No. 4,839,211 to Wilkie et al. and U.S. Pat. No. 5,058,371 to Yu et al. The carpet of Wilkie et al. is made from a blend of conventional carpet fibers (e.g., nylon fibers) and high shrinkage fibers (e.g., acrylic fibers). However, the addition of such high shrinkage fibers causes non-uniformity in the yarn and in the carpet made therefrom.

The carpet of Yu et al. is made of singles yarn having little or no twist which are cabled together. The yarns are prepared by inserting bundles of high shrinkage filaments into a conventional bulked (i.e., crimped) continuous filament singles carpet yarns by means of an air tangler. The yarn is then heatset. During heatsetting of the yarn, the bundles of high shrinkage filaments cause the crimped continuous filament singles carpet yarns to buckle. Some breakage of the high shrinkage acrylic filaments may occur by this method because the acrylic filaments are fragile. Also, as in Wilkie et al., the addition of high shrinkage filaments in the yarn of Yu et al. causes non-uniformity in the yarn and in the carpet made therefrom.

A carpet having a tightly tailored surface texture is a particular type of trackless carpet. The term "tightly tailored surface texture" as used herein means a surface texture characterized by substantially straight and unkinked tufts having a tightly twisted structure, with great twist integrity. The tuft tips are substantially unopened and have compact helical curls, and the tuft structures do not demonstrate gross buckling. This texture is the result of the individual tuft structures having axial compression deformations, similar to the compression of a helical spring and is a particularly desirable texture for a carpet. Thus, there especially exists a need for creating a saxony-type carpet having a tightly tailored surface texture and for analyzing the surface texture thereof.

SUMMARY OF THE INVENTION

Accordingly, it is an object of the present invention to provide a generalized method for analyzing the texture of any surface, where the method constructs a set of normalized textural parameters which are linked to the physical properties of the surface and are independent of variations in the instruments used to measure the surface's physical properties.

It is especially desirable to use the method of the present invention to analyze the texture of a textured, saxony-type carpet, and more specifically, a saxony-type carpet having a tightly tailored surface texture.

Another object of the present invention is to make a saxony-type carpet having a tightly tailored surface texture which comprises a yarn which is uniform and which exhibits minimal breakage of the filaments thereof.

It is also an object of the present invention to make a saxony-type carpet having a tightly tailored surface texture and comprising yarn having a low ply-twist level. It is particularly desirable to make carpets using yarn having a low ply-twist level, since the yarn output product decreases as the twist level of the carpet increases. This increase thus increases the cost of making the yarn. The decrease in yarn output product also impacts the efficiency of the rest of the process for making carpet, which in turn increases the cost of making carpet.

In order to achieve the foregoing objects, there is provided a method for analyzing the texture of a surface. The method comprises the steps of preparing a first, or unknown, sample of the surface and generating at least one image of the surface of the sample. A normalized co-occurrence matrix is generated from each image for a predetermined orientation and a predetermined spatial period. At least one textural parameter is then calculated from each normalized co-occurrence matrix. A set of normalized textural parameters is constructed from the at least one textural parameter, where the normalized textural parameters are related to the physical properties of the surface. A value for each of the normalized textural parameters is then calculated. The above steps are then repeated for a second, or goal, sample, and the value for each of the normalized textural parameters for the first sample is compared to the value for the corresponding normalized textural parameters for the second sample to determine whether the first sample has a texture similar to the texture of the second sample.

It is preferable that the preparing step for the first and second samples includes preparing a sample of a carpet. It is further preferable that the preparing step for the second sample includes preparing a sample of a textured, saxony-type carpet, and it is even further preferable that the preparing step for the second sample includes preparing a sample of a textured, saxony-type carpet having a tightly tailored surface texture.

Further in accordance with the present invention, there is provided a saxony-type carpet having a tightly tailored surface texture. The carpet comprises multifilament yarn wherein the filaments of the yarn have substantially the same shrinkage values and the ply-twist level of the yarn is below about 1.67 turns per centimeter. The carpet is characterized by a set of normalized contrast parameters. The normalized contrast parameters meet the following conditions. The normalized sum of the absolute difference in contrast parameters of the sample for a first and a second position in each of a first and a second stroke direction of the sample is less than about 130, where the second position is rotated 180° from the first position, and the second stroke direction is reversed 180° from the first stroke direction. The normalized absolute difference of the absolute difference in contrast parameters for the first and the second positions for each stroke direction is in the range of about 75 to 146, and the normalized sum of the contrast parameters for the first and the second positions in each stroke direction is in the range of about 95 to 140, where a goal sample comprises a saxony-type carpet having a tightly tailored surface texture. It is preferable that the yarn has a twist level in the range of 3.0 to 4.2 turns per inch (1.18 to 1.65 turns per centimeter). It is further preferable that the yarn comprises substantially 100% crimped filaments. It is also preferable that the yarn, which may have a twist level in the range of 3.0 to 4.2 turns per inch (1.18 to 1.65 turns per centimeter) and which may comprise substantially 100% crimped filaments, may comprise either nylon 66 or nylon 6 yarn.

Further in accordance with the present invention, there is provided a saxony-type carpet having a tightly tailored surface texture. The carpet comprises multifilament yarn wherein the filaments of the yarn have substantially the same shrinkage values and the ply-twist level of the yarn is below about 1.67 turns per centimeter. The carpet is characterized by a set of normalized contrast parameters. The normalized contrast parameters meet the following conditions. The normalized sum of the absolute difference in contrast parameters of the sample for a first and a second position in each of a first and a second stroke direction of the sample is less than about 130, where the second position is rotated 180° from the first position, and the second stroke direction is reversed 180° from the first stroke direction. The normalized absolute difference of the absolute difference in contrast parameters for the first and the second positions in each stroke direction is greater than about 75, and the normalized sum of the contrast parameters for the first and the second positions in each stroke direction is in the range of about 95 to 110, where a goal sample comprises a saxony-type carpet having a tightly tailored surface texture. It is preferable that the yarn has a twist level in the range of 3.0 to 4.2 turns per inch (1.18 to 1.65 turns per centimeter). It is further preferable that the yarn comprises substantially 100% crimped filaments. It is also preferable that the yarn, which may have a twist level in the range of 3.0 to 4.2 turns per inch (1.18 to 1.65 turns per centimeter) and which may comprise substantially 100% crimped filaments, may comprise either nylon 66 or nylon 6 yarn.

BRIEF DESCRIPTION OF THE DRAWINGS

The accompanying drawings, which are incorporated in and constitute a part of the specification, illustrate the presently preferred embodiments of the invention, and together with the general description given above and the detailed description of the preferred embodiments given below, serve to explain the principles of the invention.

FIG. 13 is a table showing two normalized contrast parameters of a sample of a carpet having a tightly tailored surface texture according to the present invention and a straight-set, saxony-type carpet of the prior art measured under varying light intensity conditions as described in Example 5.

FIG. 14 is a table showing three normalized contrast parameters of samples of carpet of the prior art and of the present invention imaged in two opposite positions and two opposite stroke directions as described in Example 5.

FIG. 15 is a table showing the results of a reproducibility test performed on a straight-set, saxony-type carpet of the prior art as described in Example 5.

DESCRIPTION OF THE PREFERRED EMBODIMENTS

Figure 1:
FIG. 1 is a photograph of a carpet made to develop a Visual Rating Scale using currently commercially available yarn and known methods and which has a frieze surface texture and a Visual Rating of 1.
Figure 2:
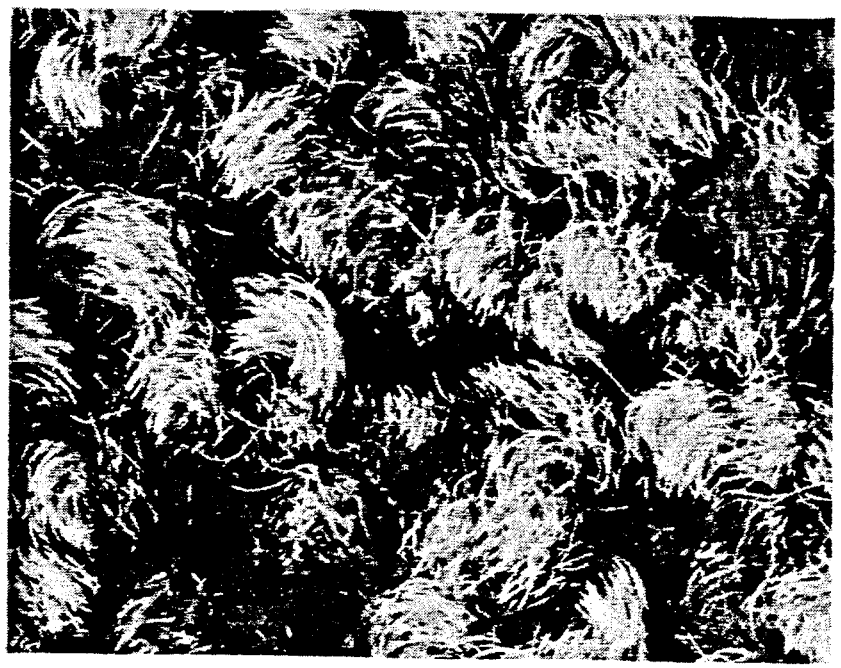
FIG. 2 is a photograph of a carpet made to develop the Visual Rating Scale using currently commercially available yarn and known methods and which has a surface texture between the frieze texture of the carpet in FIG. 1 and the texture of the carpet shown in FIG. 3 and a Visual Rating of 2.

Reference will now be made in detail to the present preferred embodiments of the invention as illustrated in the accompanying drawings.

In accordance with the present invention, there is provided a method of analyzing the texture of a surface. The method comprises the step of preparing a first, or unknown, sample of the surface. In one embodiment of the present invention, hereinafter referred to as "the carpet embodiment", the preparing step for the first sample comprises preparing a sample of any type of carpet, which may be, but is not limited to, any frieze or saxony-type carpet of the prior art, or a textured, saxony-type carpet having a tightly tailored surface texture of the present invention.

An improved process for texturing a "ply-twisted crimped multifilament yarn" to make a carpet having a tightly-tailored surface texture is disclosed in the '353 application, noted above, and hereinbelow. As used herein, the term "ply-twisted crimped multifilament yarn" means a multifilament yarn constructed by cabling together two or more singles yarns, either by a two-step twisting/cabling process or a direct cabling process, both of which are familiar to one skilled in the art. Preferably, the yarn is comprised of bulked continuous filament (BCF) yarns. Staple spun yarns may also be used.

The ply-twisted crimped multifilament yarn used in the process described herein may be composed of any polymeric material capable of undergoing a heat-setting operation, e.g., polyamides, polyesters, polyolefins and acrylonitriles. Polyamides, such as nylon 66 and nylon 6, are especially suitable. Polyamides containing at least 80% by weight of nylon 66, where the remaining portion is a polymer made from a polyamide monomer, such as 2-methylpentamethylenediamine (MPMD), caprolactam, etc., are also suitable. The polyamide containing at least 80% by weight of nylon 66 may be a true copolymer or melt blend.

It is also preferable that the total denier of the ply-twisted yarn be in the range of about 2000 to 4000, and that the denier of each filament yarn be in the range of about 10 to 20 denier per filament (dpf). The cross-section of each filament yarn may be circular, hollow, especially as described in Champaneria et al., U.S. Pat. No. 3,745,061, trilobal, or any other non-round shape. Preferably, the modification ratio (MR) of the trilobal filaments is less than about 2.4. The singles yarn may have bulk crimp elongation (BCE) from about 10% to 45%. It is preferable, for the purposes of the invention, that the singles yarns have a BCE greater than about 30%.

Those skilled in the art are familiar with the following methods used to texture and heat-set the twist in the multifilament yarn, and these methods may be generally used in the process described herein. Initially, the multifilament yarn is fed through a stuffer box, where the yarn is compressed. The stuffer box typically includes two friction feed rolls which force the yarn into a cavity, while a restrained gate exerts rearward pressure on the yarn. The operating conditions for the stuffer box, such as gate pressure, may be adjusted accordingly.

The multifilament yarn may then pass through a continuous heat-setting machine, known as a Superba ®. Generally, in such an operation, the multifilament yarn is placed onto a conveyor belt which first moves through an atmospheric steam pre-bulking chamber, and then through the heat-setting chamber. In the pre-bulking chamber, the yarn is heat-relaxed in order to develop bulk in the yarn. In the heat setting chamber, the yarn is treated with pressurized saturated steam to heat-set the twist and mechanically stabilize the yarn structure. For nylon 66 multifilament yarns, the temperature is generally in the range of about 125° to 135° C. The bulked, multifilament yarn is then dried.

Alternatively, the multifilament yarn may pass through a continuous heat-setting machine, known as a Suessen. The Suessen treats the yarn with dry heat to heat-set the twist. For nylon 66 multifilament yarns, the temperature is generally in the range of about 185° to 205° C. The multifilament pile yarn is then tufted into the backing of a carpet, cut and sheared by procedures known in the art. The resulting tufts provide a specific surface texture for the carpet.

The particular surface texture for a carpet is dependent upon several factors including the ply-twist level, twist structure, twist integrity, diameter, helix angle, and radius of curvature of the tufts formed by the multifilament pile yarn. The contribution of the stuffer box is also critical, since it helps to create the desirable surface texture by the type and degree of axial compression and deformation which it imparts to the multifilament yarn. The type and degree of deformation which is permanently introduced into the multifilament yarn is also dependent upon the bending modulus and recovery of the individual fibers at the time of deformation. In turn, these fiber properties are determined to a great extent by the particular polymer which composes the fibers.

The yarn is saturated with water and the saturated yarn is preheated to a temperature in the range of about 40° to 90° C. immediately before the yarn is fed through the stuffer box. By the term "saturated", it is meant that there is water present in excess of that which will be actually absorbed into the fiber. For nylon 66, this corresponds to greater than approximately 9% water by weight based on the dry weight of the yarn. It is believed that increasing the temperature and moisture content of the multifilament yarn immediately prior to the yarn entering the stuffer box causes the yarn to more permanently accept the deformation imparted by the stuffer box. The multifilament yarn is preheated by such means as, for example, impinging pressurized heated fluid on the yarn. The heated fluid may be, for example, hot air, dry steam, or saturated steam. If polyamide yarns are to be treated, saturated steam is preferably used. Preferably, the yarn is simultaneously saturated and preheated by means of saturated steam.

Figure 7:
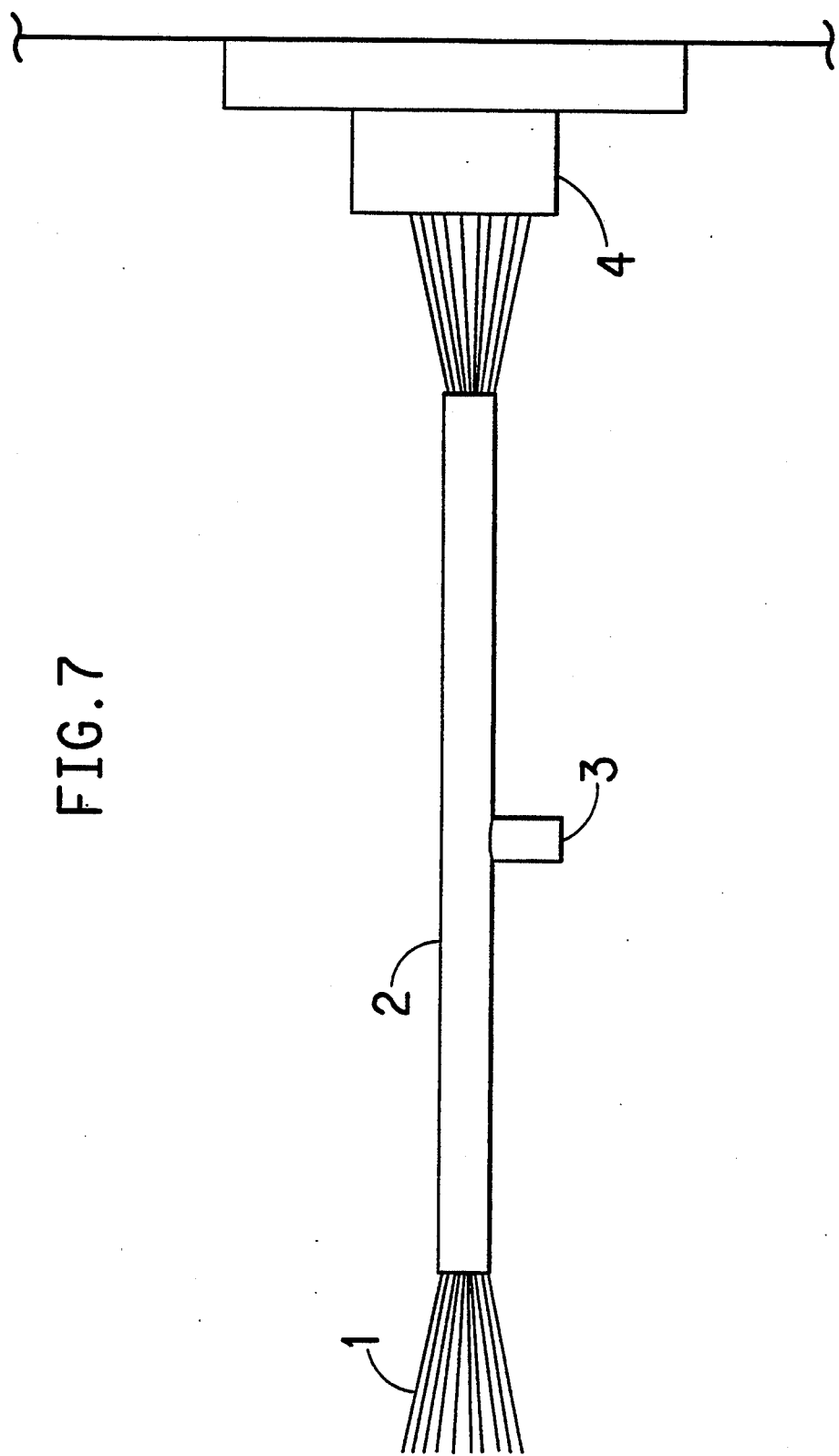
FIG. 7 is a side view of a steam tube used in the process for making a saxony-type carpet of the present invention which has a tightly tailored surface texture as shown in FIG. 8.

A preferred apparatus for treating the yarn with saturated steam is shown in FIG. 7. Referring to FIG. 7, a multifilament yarn 1 is fed into a steam tube 2. The steam tube is insulated and includes a steam inlet 3. Steam is supplied to the tube by an insulated steam line. The length of the tube is sufficient such that there is enough time to uniformly heat and saturate the bundle of ply-twisted yarns. The inside diameter of the tube is approximately the same diameter as the loosely consolidated bundle of yarns which are conditioned at one time. The yarn then exits the tube and enters a stuffer box inlet 4 as shown in FIG. 7. The steam tube as shown in FIG. 7 is one example of a suitable device for practicing this invention. However, it is recognized that those skilled in the art will be aware of other suitable devices.

Figure 8:
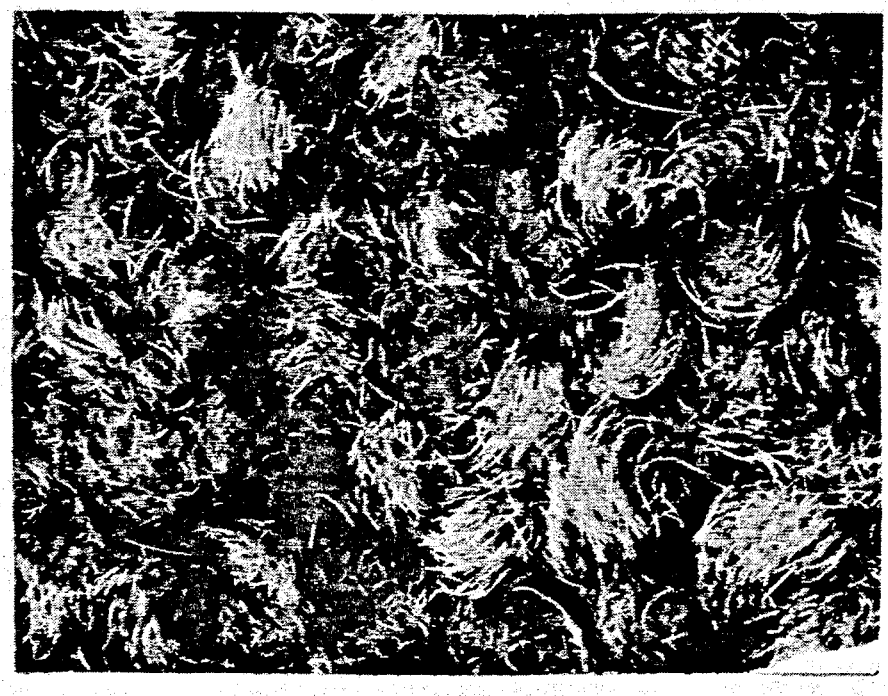
FIG. 8 is a photograph of a saxony-type carpet of the present invention which has a tightly tailored surface texture made by the steam tube as shown in FIG. 7.

The process described with respect to FIG. 7 provides new multifilament yarns which can be tufted by techniques known in the art into a carpet having a tightly tailored surface texture as shown in FIG. 8. The filaments of these yarns have substantially the same shrinkage values. Also, the ply-twist level of the yarn is below about 4.25 turns per inch (1.67 turns per centimeter). More preferably, the yarn has a ply-twist level in the range of about 3.0 to 4.2 turns per inch (1.18 to 1.65 turns per centimeter). An advantage of the process described with respect to FIG. 7 is that a multifilament yarn having an initial ply-twist level below about 4.25 turns per inch (1.67 turns per centimeter) may be treated, and the resulting yarn will substantially retain its twisted structure. It should be noted that the ply-twist level of the finished carpet is slightly greater than the ply-twist level of the yarn used to make the carpet (i.e., the input ply-twist level). The input ply-twist level of the carpet shown in FIG. 8 is about 4.03 turns per inch (1.54 turns per centimeter). Preferably, the multifilament yarn produced by the process described with respect to FIG. 7 includes substantially 100% crimped filaments. This multifilament yarn is a polyamide yarn. The yarn may comprise at least 80% by weight of nylon 66. Alternatively, the yarn may comprise nylon 6.

The carpets of FIGS. 1-6 were made to develop a Visual Rating Scale. In the formulation of the Visual Rating Scale, the surface texture of various carpet samples were visually compared in a side-by-side comparison without knowledge of which carpets were made from which yarns. The carpets were examined by a panel of people familiar with carpet construction and surface textures. The carpets were given a rating of 1 to 6, where 1-6 represent known surface textures. Ratings were based on the overall surface texture of the carpet, which in turn was based on such factors as ply-twist level, structure, integrity, presence of compact helical curls at tuft tips, and/or gross buckling of tuft structures.

Figure 6:
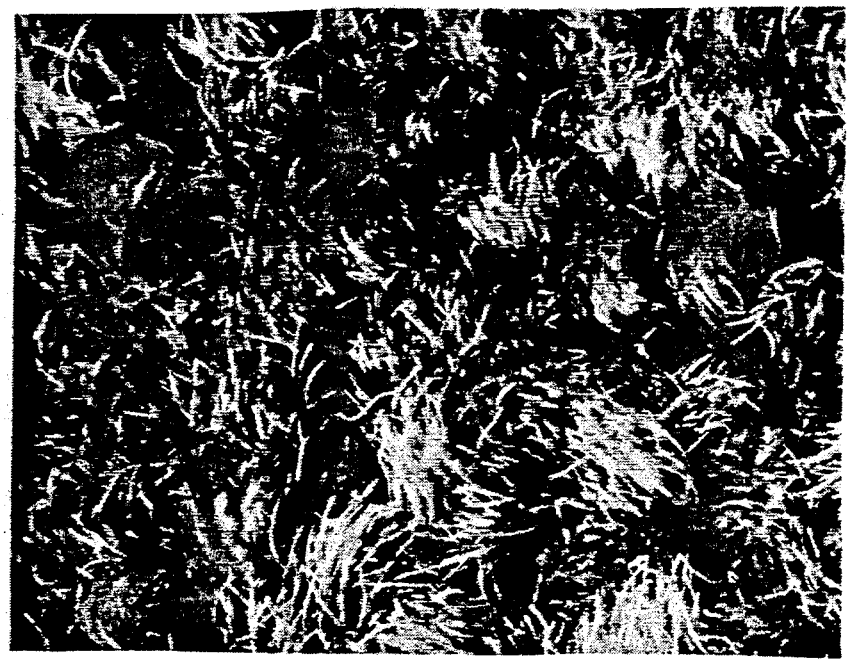
FIG. 6 is a photograph of a carpet made to develop the Visual Rating Scale using currently commercially available yarn and known methods and which has a loose surface texture, with open tuft tips forming a brush-like appearance and a Visual Rating of 6.

The carpet shown in FIG. 1 was made using currently commercially available yarn and known methods and has a frieze surface texture. The carpet shown in FIG. 2 was made using currently commercially available yarn and known methods and has a surface texture between the frieze texture of the carpet of FIG. 1 and the texture of the carpet shown in FIG. 3. The carpets of FIGS. 1 and 2 have a surface texture with a substantial amount of highly-kinked tuft structures which demonstrate gross buckling and were given a rating of 1 and 2, respectively on the Visual Rating Scale. The carpet shown in FIG. 5 was made using currently commercially available yarn and known methods and has a surface texture between the texture of the carpet of FIG. 4 and the texture of the carpet shown in FIG. 6. The carpet shown in FIG. 6 is made using commercially available yarn and known methods and has a loose surface texture, with open tuft tips forming a brush-like appearance. The carpets shown in FIGS. 5 and 6, were given a rating of 5 and 6, respectively, on the Visual Rating Scale.

Figure 3:
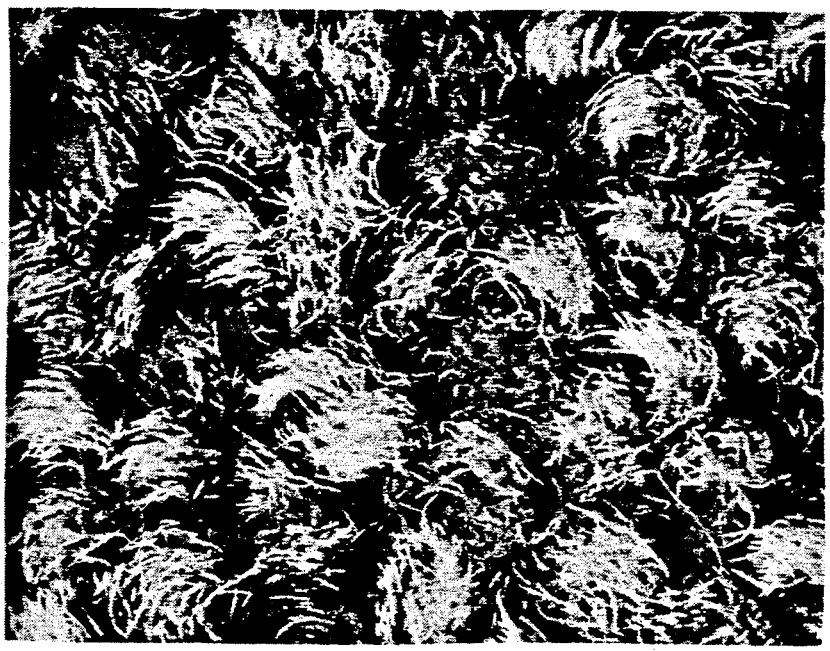
FIG. 3 is a photograph of a carpet made to develop the Visual Rating Scale using currently commercially available yarn and known methods and which has a tightly tailored surface texture and a Visual Rating of 3.
Figure 4:
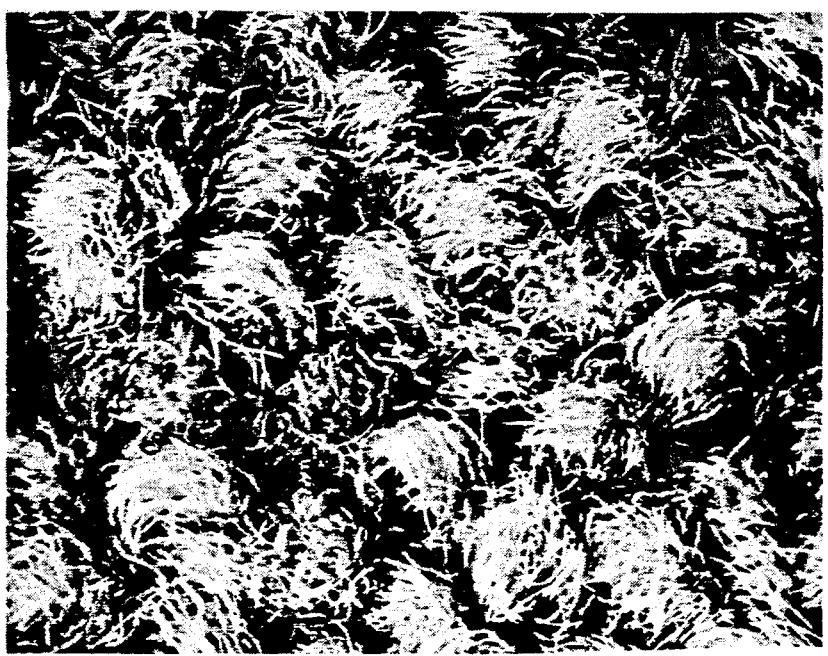
FIG. 4 is a photograph of a carpet made to develop the Visual Rating Scale using currently commercially available yarn and known methods and which has a tightly tailored surface texture and a Visual Rating of 4.
Figure 5:
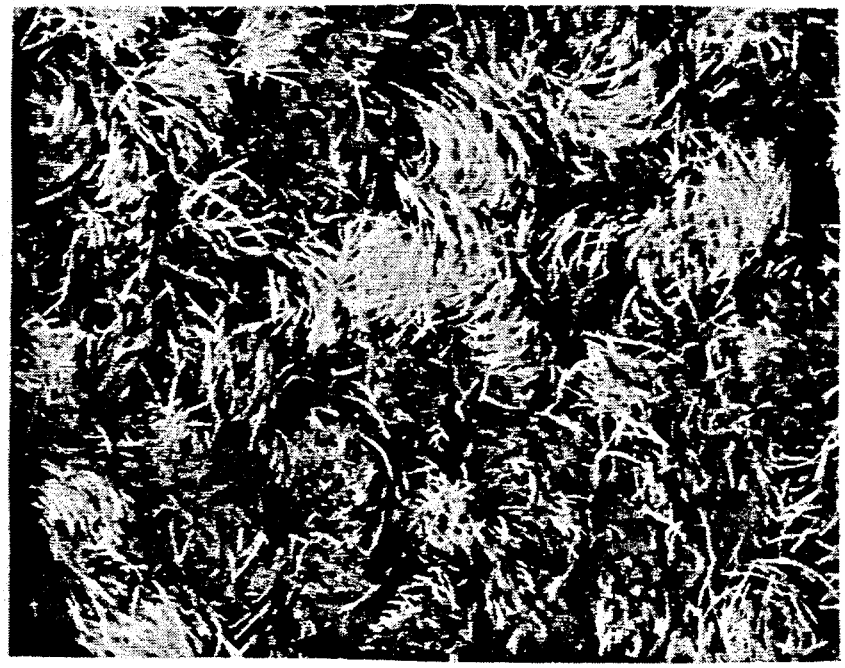
FIG. 5 is a photograph of a carpet made to develop the Visual Rating Scale using currently commercially available yarn and known methods and which has a surface texture between the texture of the carpet of FIG. 4 and the texture of the carpet shown in FIG. 6 and a Visual Rating of 5.

The carpets shown in FIGS. 3 and 4, like that shown in FIG. 8, have a tightly tailored surface texture and were given a rating of 3 and 4, respectively on the Visual Rating Scale. The carpets of FIGS. 3 and 4 were made using currently commercially available yarn and known methods. Specifically, the carpets shown in FIGS. 3 and 4 were made from 1480 denier high bulk (35% BCE) nylon 66 bulked continuous filament (BCF) singles yarn, sold by E.I. du Pont de Nemours and Company of Wilmington, Delaware (hereinafter referred to as "Du Pont") as 1480/P943 "Fiber for Stainmaster$^{cm}$ Carpets". This yarn was tufted into carpet using trade-accepted practices which used no steam in the stuffer box. The BCF yarn was twisted on a Yolkman twister, was heat-set and was textured on a Superba® stuffer box at standard conditions (i.e., 132° C. with no steam used in the stuffer box). The carpet was then tufted on an eight-gauge, cut-pile tufting machine and was then dyed, latexed and sheared. The ply-twist level of the carpet shown in FIG. 3 is about 5.5 turns per inch (2.17 turns per centimeter). The ply-twist level of the carpet shown in FIG. 4 is about 4.25 turns per inch (1.67 turns per centimeter).

Figure 9:
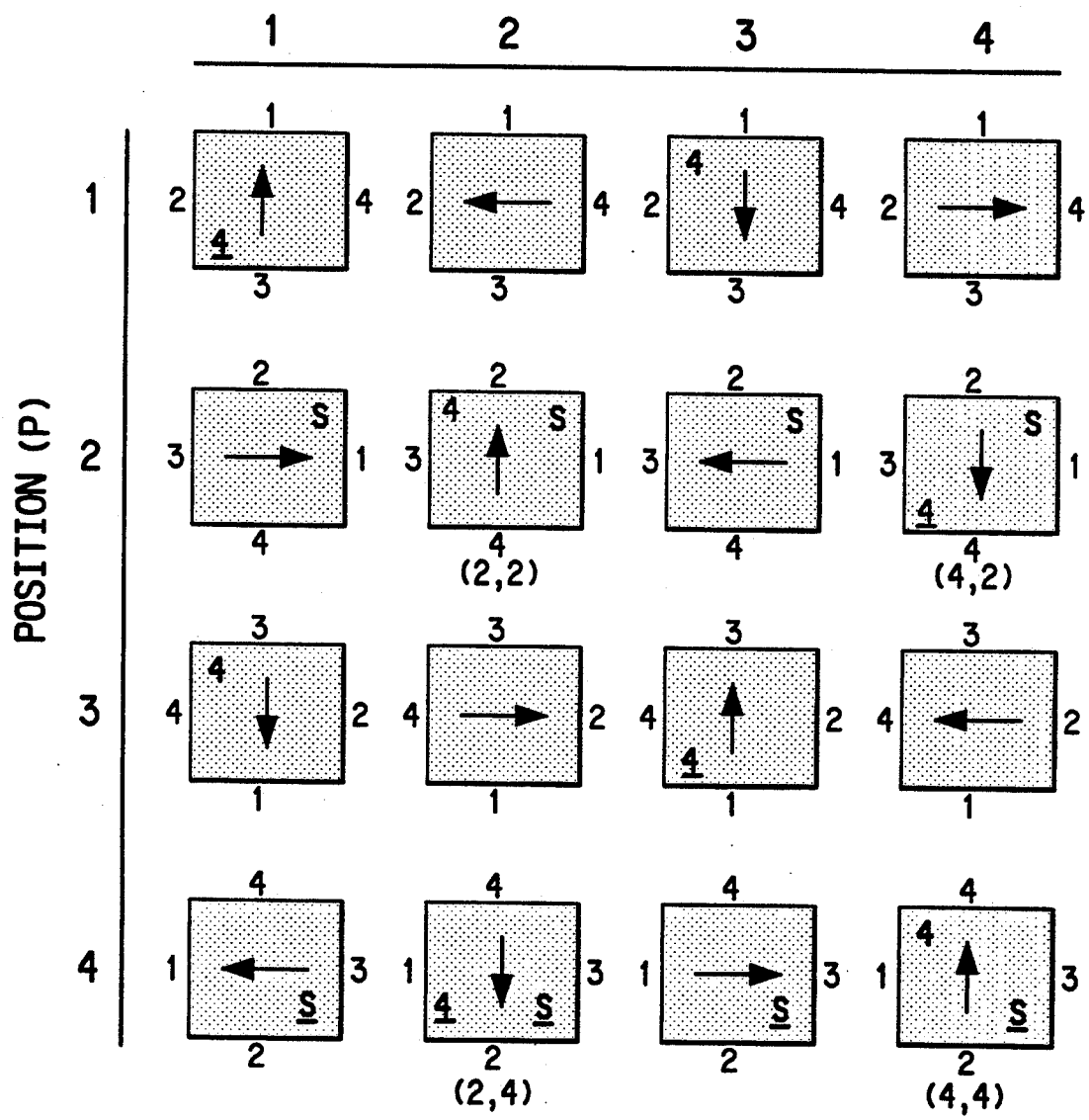
FIG. 9 is a schematic diagram showing sixteen different stroke direction and position combinations for analyzing a sample of a straight-set, saxony-type carpet of the prior art and a sample of the carpet having a tightly-tailored surface texture as shown in FIG. 4 using the method of the present invention.

Referring again to the method for analyzing the texture of a surface, the preparing step for the carpet embodiment of the present invention includes the sub-steps of stroking the carpet in a plurality of predetermined stroke directions and positioning the sample of carpet in a plurality of positions. FIG. 9 is a schematic diagram illustrating sixteen different combinations of stroke directions and positions for two samples of carpet from which four preferred combinations are selected to carry out the analysis. The two samples represent a straight-set, saxony-type carpet of the prior art (SAX) and the saxony-type carpet having a tightly tailored surface texture of the present invention as shown in FIG. 4 and which is made as described above (S$_4$). In FIG. 9, the dots represent the tufts of the carpet. S represents the maximum brightness for a given stroke direction over four positions for SAX, and 4 is the maximum brightness for a given stroke direction over four positions for S$_4$. Also, S represents the minimum brightness for a given stroke direction over four positions for SAX, and 4 represents the minimum brightness for a given stroke direction over four positions for S$_4$. The brightness of the carpet samples is defined as the average gray level pixel intensity for a given image under constant experimental conditions. The four stroke direction and position combinations used for subsequently deriving the normalized set of textural parameters are denoted by the coordinates (2,2), (4,2), (2,4) and (4,4) as shown in FIG. 9. The four selected combinations denoted in FIG. 9 were chosen because they represent the maximum difference in brightness between SAX and S$_4$. The tuft axis for all combinations is along the 2–4 direction in FIG. 9.

Figure 10:
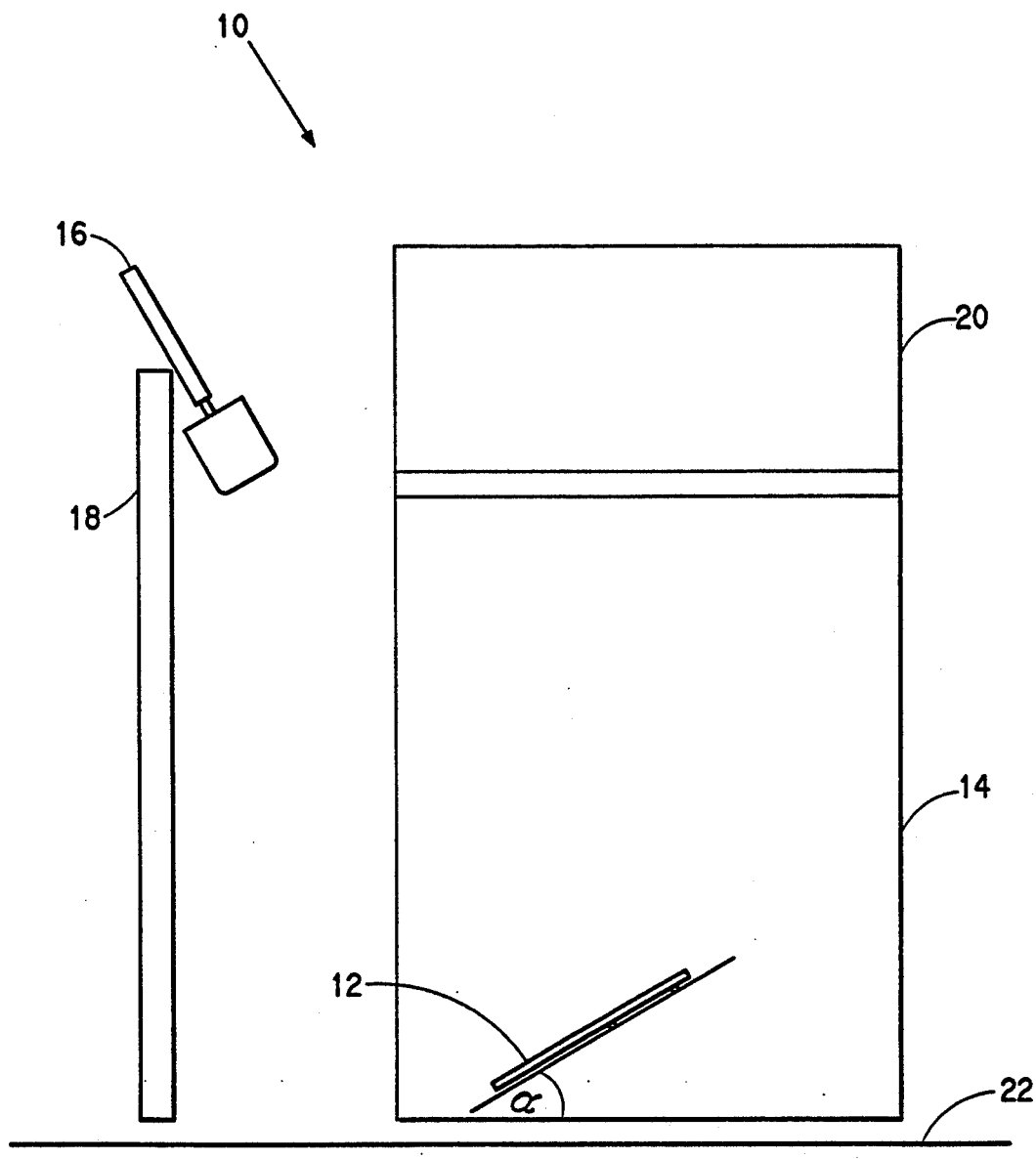
FIG. 10 is a schematic view of the equipment used to generate an image of the samples of carpet.

The method of the present invention also comprises the step of generating at least one image of the first sample. A system for generating the image of the sample is shown generally at 10 in FIG. 10. System 10 comprises a sample 12 which is held in a sample holder 14. System 10 also comprises a camera 16 which generates an image of the sample and which is held on a stand 18, and a light illumination source 20 for illuminating the sample. Sample holder 14 and stand 18 rest on a base as shown in FIG. 10. In a preferred embodiment, the camera is a charge-coupled device (CCD) camera, although any type of camera, or more generally, any type of device for generating an image may be used. Preferably, the sample is oriented so that the axis of the tufts of the sample is at an oblique angle with respect to light illumination source 20. As shown in FIG. 10, the sample is oriented at an angle, $\alpha$, with respect to the base of the sample holder, where $\alpha$ is preferably about 25°. Thus, the axis of the tufts of the sample is oriented at an angle, $90-\alpha$, with respect to the light illumination source, where the angle is preferably about 65°.

In the carpet embodiment, the steps of preparing a first sample of the surface and of generating at least one image of the sample include the following sub-steps. First, the axis of the tufts of the sample is established. The carpet is then stroked in a plurality of predetermined stroke directions and is positioned in a plurality of predetermined positions. Specifically, the sample is stroked in a first direction along the axis of the tufts. The sample is oriented to a first position so that the axis of the tufts is perpendicular to and the tufts face the viewing direction of the camera used to generate the image of the surface of the sample, such as camera 16 in FIG. 10, and so that the axis of the tufts is at an oblique angle, which is preferably about 65°, to the light illumination source which is used to illuminate the sample, such as source 20 as shown in FIG. 10. A first image of the sample is then generated. The sample is then rotated by 180° to a second position so that the axis of the tufts remains perpendicular to and the tufts face the viewing direction of the camera and so that the axis of the tufts is at an oblique angle, which is preferably about 65°, to the light illumination source. A second image of the sample is then generated. The sample is then stroked in a second direction 180° in the opposite direction of the first direction along the axis of the tufts. The sample is then oriented to the second position so that the axis of the tufts is perpendicular to and the tufts face the viewing direction of the camera and so that the axis of the tufts is at an oblique angle, which is preferably about 65°, to the light illumination source. A third image of the sample is then generated. The sample is then rotated 180° to the first position so that the axis of the tufts remains perpendicular to and the tufts face the view direction of the camera and so that the axis of the tufts is at an oblique angle, which is preferably about 65°, to the light illumination source. A fourth image of the sample is then generated.

The method also comprises the step of generating at least one normalized co-occurrence matrix from each image for a predetermined orientation and a predetermined spatial period. Each element in the normalized co-occurrence matrix represents the probability of co-occurrence for a predetermined gray level pair of pixels in the image. The image analysis model used in the present invention is based on the second order co-occurrence matrix model originally developed by Haralick, et al., supra. This model is based on examining the statistics of the spatial relationship between gray levels in a homogeneously textured image. The fundamental data structure in the Haralick model is the second order gray level co-occurrence matrix $\|P\|$. The matrix elements $P_{ij}$ of this matrix for a given spatial period, d, represents the probability of co-occurrence of gray levels i and j spaced apart by a given distance parameter. The application of the Haralick model to carpet wear assessment is described in Siew et al., supra. It should be noted that instead of generating a co-occurrence matrix, a difference co-occurrence matrix as described in Siew et al., supra, and Sobus et al., supra, may be generated.

The method of the present invention also comprises the step of calculating at least one textural parameter from each normalized co-occurrence matrix. The textural parameter may be a Haralick textural parameter. Haralick lists fourteen textural parameters derived from the co-occurrence matrix. Many of the Haralick parameters are measures of local contrast/homogeneity of the surface being analyzed. Other textural parameters can also be derived from the co-occurrence matrix.

It should be noted that a co-occurrence based textural model is a general way of analyzing a large range of statistical, homogeneous textures. The textural parameters which are computed may be application specific. However, the ability of the model to calculate parameters for different spatial frequencies in different applications makes it a powerful tool. To implement this model in the method of the present invention, it is important to construct normalized parameters which are robust against instrumental variations and tonal variations in the sample. In addition, selection of the appropriate spatial frequency window is necessary for calculating a physically meaningful parameter. In principle, if one follows these guidelines, one can implement the co-occurrence based textural model to analyze finished surfaces and other commercially important materials, as well as carpet surfaces.

The step of calculating at least one textural parameter comprises calculating a contrast parameter for each of the first through fourth images, respectively. The contrast parameter, which is one of the fourteen Haralick parameters, has been found to be especially useful for analyzing the texture of carpets. This parameter is defined as follows:

$$C = \sum_{n=0}^{N_{gray}-1} n^2 \left\{ \sum_{i=1}^{N_{gray}} \sum_{j=1}^{N_{gray}} P_{ij} \right\} \quad (1)$$

$$|i - j| = n$$

The contrast parameter is a difference moment of the co-occurrence matrix and measures the local variations in gray level present in an image. This variation is measured over the spatial period being used. The weighting of the contrast parameter by the factor $n^2$ indicates that as the local variation in gray levels rises, the contrast parameter should rise rapidly.

The step of calculating the at least one textural parameter comprises the sub-steps of calculating the textural parameters for each integral increment of the spatial period range and averaging the textural parameters over all the integral increments of the range of the spatial period. The spatial period of a tuft is an integral value and is in the range of $1.8n \pm n/2$, where n is the spatial distance in pixels between the center of the one tuft and the center of an adjacent tuft. Spatial frequency plays a role in calculating textural parameters for carpets. For example, in calculating the contrast parameter, if the spatial frequency used in the analysis is much greater than the tuft spatial frequency, the calculated contrast parameter will be a measure of local variations within a tuft rather than between a tuft and a void. If the spatial frequency is much lower than the tuft frequency, the results are susceptible to longer range defects on the carpet surface, which introduces lower frequency textural correlations.

It is important to note that the base spatial period may comprise other values. In the carpet embodiment of the present invention, the base spatial period is about 1.8 times the tuft spatial period. The base spatial period is desired to be in and around the tuft frequency, so that the tuft-to-void contrast is analyzed. The factor 1.8 was chosen to minimize "periodicity" noise by avoiding analyzing the texture at integral harmonics of the tuft frequency. In addition, the contrast parameter is averaged over one full tuft width to ensure that at each point being sampled in the image there would be at least one "complementary" point being used in the calculation of the contrast parameter. A complementary point for a tuft point is a void point, and vice versa. The averaging also tends to reduce random noise present in a tuft.

The normalized co-occurrence matrix is generated by a module, TRACK BATCH, and the step of calculating the at least one textural parameter from the normalized co-occurrence matrix is performed by a sub-module of TRACK BATCH, TRACK FUNC. A flow chart illustrating the steps of TRACK BATCH is shown in FIG. 11, and a flow chart illustrating the steps of TRACK FUNC is shown in FIG. 12.

Figure 11:
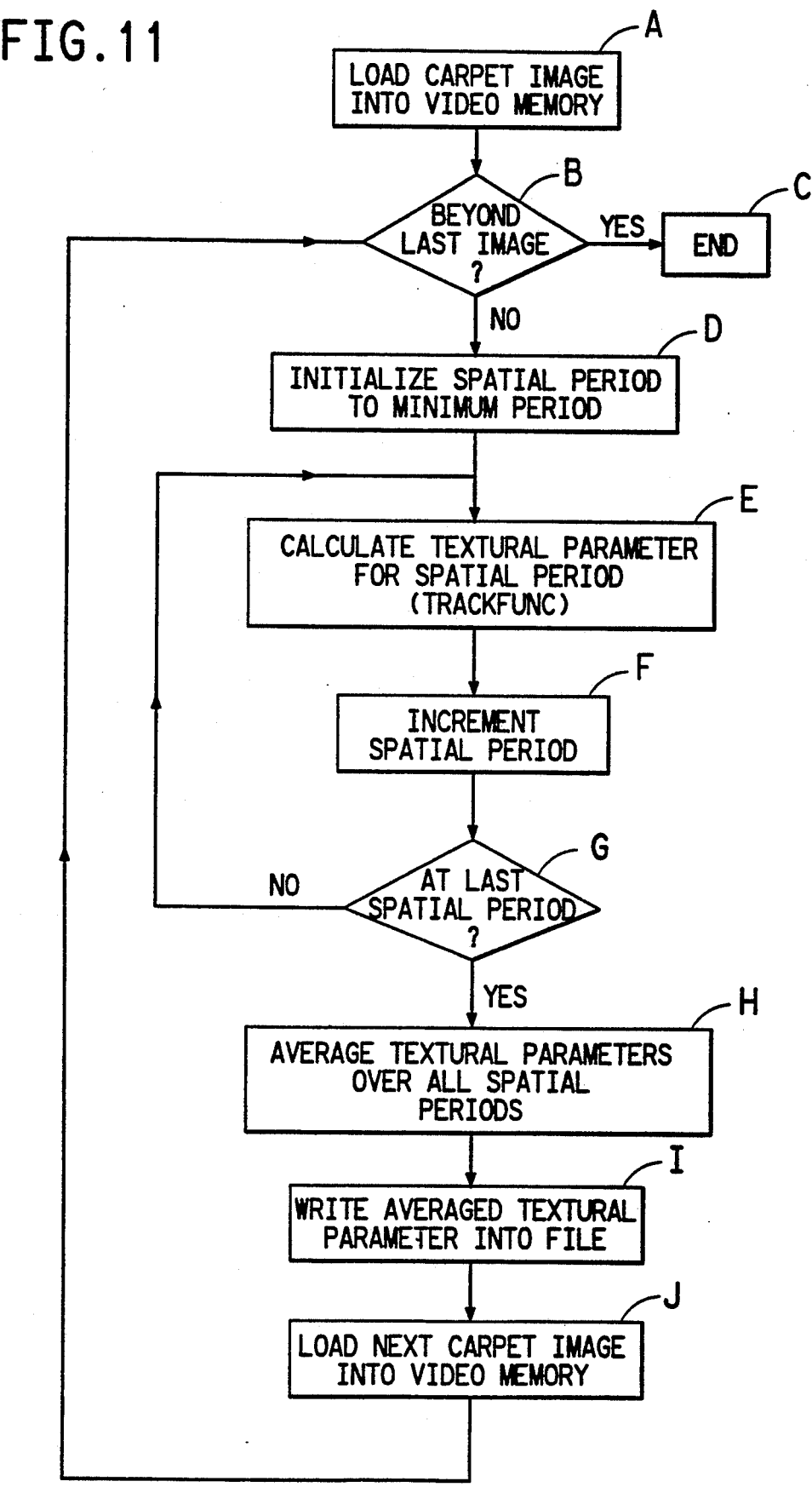
FIG. 11 is a flow chart showing the steps of a module, TRACK BATCH, which is used to generate at least one normalized co-occurrence matrix from each image of the sample.
Figure 12:
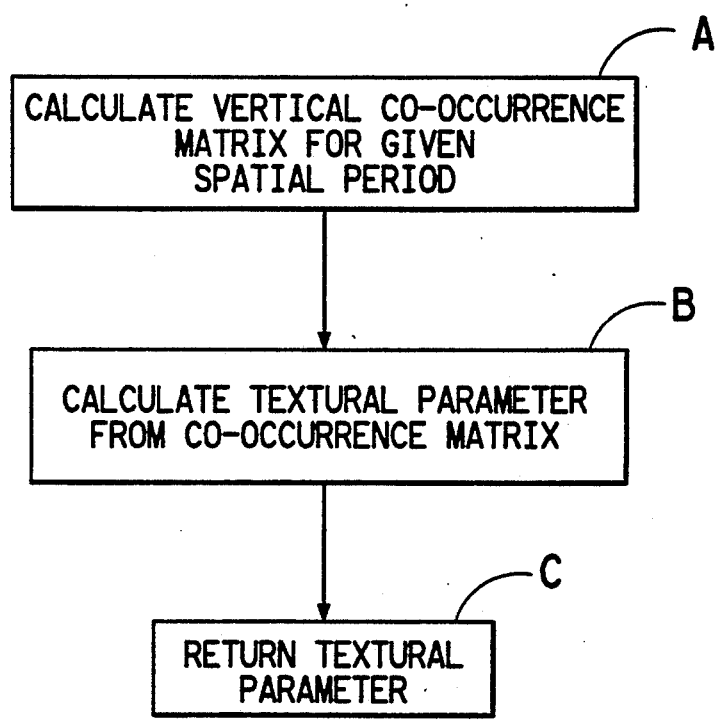
FIG. 12 is a flow chart showing the steps of a submodule of TRACK BATCH, TRACK FUNC, which is used to calculate at least one textural parameter from the normalized co-occurrence matrix generated by TRACK BATCH.

As shown in block A of FIG. 11, the first step of TRACK BATCH is to load the carpet image into a video memory, which resides in a computer. Then the question in decision diamond B asks whether TRACK BATCH is beyond the last image. If so, the module ends as shown in block C. If not, the spatial period is initialized to a minimum period, as shown in block D. In the present invention, the minimum spatial period is defined as:

$$(1.8 \times \text{tuft period} - \text{tuft period}/2) \quad (2)$$

The next step of TRACK BATCH is to calculate the at least one textural parameter for a spatial period as shown in block E of FIG. 11. This is done by the sub-module TRACK FUNC, the steps of which will be described in detail below. The spatial period is then incremented, as shown in block F. The question in decision diamond G then asks whether TRACK BATCH is at the last spatial period. The last spatial period is defined as:

$$(1.8 \times \text{tuft period} + \text{tuft period}/2) \quad (3)$$

If the answer to the question in decision diamond G is no, then TRACK BATCH returns to block E, and the at least one textural parameter for the spatial period is calculated. The spatial period is incremented again as shown in block F until TRACK BATCH is at the last spatial period as defined in equation (5) above. If the answer to the question in decision diamond G is yes, then the textural parameters are averaged over all the spatial periods as shown in block H. The averaged textural parameters are then written into a file as shown in block I, and the next carpet image is loaded into video memory as shown in block J. TRACK BATCH then returns to decision diamond B and asks whether it is beyond the last image. If so, the module stops running. If not, the loop through B-J continues until TRACK BATCH is beyond the last image.

As noted above, the step of calculating the at least one textural parameter from each normalized co-occurrence matrix is performed by the module TRACK FUNC, as illustrated in FIG. 12. As shown in block A of FIG. 12, the first step of TRACK FUNC is to calculate the vertical co-occurrence matrix for a given spatial period. TRACK FUNC then calculates the textural parameter from the vertical co-occurrence matrix as shown in block B. Finally, TRACK FUNC returns the textural parameter as shown in block C.

The method of the present invention also comprises the step of constructing a set of normalized textural parameters from the at least one textural parameter. In order for a derived textural parameter to be robust, or invariant, over a range of different carpet colors and lusters, as well as over a range of illumination and viewing conditions, it is necessary to normalize appropriately. The method of the present invention normalizes the contrast parameter so that it can handle a wide range of samples and still obtain a valid textural measure. The normalized textural parameters are related to the physical properties of the surface, such as pile lay in the carpet embodiment, and are independent of any variations in the instruments used to generate the image of the surface. In the carpet embodiment of the present invention, texture is assumed to be independent of the color or luster of the sample of carpet which is analyzed.

As noted above, the contrast parameter is the textural parameter used for the carpet embodiment of the present invention. In this embodiment, four contrast parameters averaged over the selected spatial periods are derived from four images of the sample taken over a first and a second position reversed by 180° and over a first and a second stroke direction reversed by 180° as described above. The four contrast parameters are defined as $\bar{c}_1$, $\bar{c}_2$, $\bar{c}_3$ and $\bar{c}_4$, where $\bar{c}_1$ and $\bar{c}_2$ are contrast parameters for the first stroke direction, and $\bar{c}_3$ and $\bar{c}_4$ represent contrast parameters for the opposite, or second, stroke direction.

The method of the present invention also comprises the step of calculating a value for each of the normalized textural parameters. The step of calculating a value for each of the normalized textural parameters comprises the sub-step of calculating a normalized sum of the absolute difference (NSD) in contrast parameters for the first position and the second position in each of the first and the second stroke directions of the sample, where the second position is reversed 180°, from the first position and the second stroke direction is rotated 180° from the first stroke direction. The calculating step further includes the sub-steps of calculating the normalized absolute difference of the absolute difference (NDD) in contrast parameters for the first and second positions in each of the first and second stroke directions and calculating a normalized sum (NS) of the contrast parameters for the first and second positions in each of the first and second stroke directions. The values for each of the normalized textural parameters, NSD, NDD and NS, are given by the following equations:

$$NSD = (|c_1 - c_2| + |c_3 - c_4|)/(c_1 + c_2 + c_3 + c_4) \times k_1 \quad (4)$$

$$NDD = |(|c_1 - c_2| - |c_3 - c_4|)|/(c_1 + c_2 + c_3 + c_4) \times k_2 \quad (5)$$

$$NS = (c_1 + c_2 + c_3 + c_4)/(c_{1g} + c_{2g} + c_{3g} + c_{4g}) \times k_3 \quad (6)$$

where $\bar{c}_{1g}$, $\bar{c}_{2g}$, $\bar{c}_{3g}$ and $\bar{c}_{4g}$ represent four contrast parameters, respectively, for a second, goal, or known, sample. In the carpet embodiment of the present invention, $k_1$ was set to 400, $k_2$ was set to 1000, and $k_3$ was set to 100 in order that the values NSD, NDD and NS could be easily compared in a side-by-side comparison.

It should be noted that the values NSD and NDD for the first, or unknown sample, are independent of NSD and NDD for the second, or goal sample. NS of the unknown sample does depend on performing measurements for NS on the goal sample. However, the instrumental conditions under which values for the contrast parameters for the goal sample are measured are identical to those conditions under which the contrast parameters for the unknown sample are measured. In addition, in the carpet embodiment, the goal sample of carpet must have the same luster and color as the unknown sample of carpet.

The value NSD, when calculated for the carpet embodiment of the present invention, essentially measures the tendency of the tufts of a carpet to "lay over" in a preferred orientation when stroked in both directions. For a saxony-type carpet having a tightly tailored surface texture of the present invention, it has been found that for one stroke direction there was a tendency of the tufts of the carpet to "lay over". For the opposite stroke direction, this was not true. This implies that the pile lay of saxony-type carpets having a tightly tailored surface texture is directional, as the tendency of the carpet tufts to "lay over" is enhanced in certain stroke directions. In contrast, it has been found that for straight-set, or non-textured, saxony-type carpets of the prior art, there is a tendency for the carpet tufts to "lay over", regardless of the stroke direction. The "lay-over" tendency for the tufts of a straight-set, saxony-type carpet of the prior art is high for both stroke directions, resulting in a larger value of NSD. Normalizing by the factor $(\bar{c}_1 + \bar{c}_2 + \bar{c}_3 + \bar{c}_4)$ ensures that NSD will not vary significantly over wide instrumental variations.

In the carpet embodiment of the present invention, the directionality of the "lay over" tendency for the tufts of the saxony carpet having a tightly tailored surface texture of the present invention results in larger values of NDD for this carpets. In contrast, NDD for straight-set, saxony carpets of the prior art is small, since there is no strong directionality in the tendency of the tufts of these carpets to "lay over".

In the carpet embodiment of the present invention, NS is a measure of the total contrast of the carpet, normalized to the total contrast of the goal sample. Thus, NS depends on the goal sample used and more specifically, on the overall tuft geometry of the sample, as it is a measure of the local contrast of a tuft with respect to a neighboring void.

The method of the present invention also comprises the step of repeating the steps of preparing the sample, generating at least one image of the sample, generating at least one normalized co-occurrence matrix from each image, calculating at least one textural parameter, constructing a set of normalized textural parameters and calculating a value for the normalized textural parameters for a second, or goal, sample. In the carpet embodiment of the present invention, the repetition of the preparing step for the second sample comprises preparing a textured saxony-type carpet, and more preferably a saxony-type carpet having a tightly tailored surface texture.

The values NSD, NDD and NS allow one to predict in what way a saxony-type carpet of the prior art fails the criteria for a saxony-type carpet having a tightly tailored surface texture of the present invention. This may be especially useful in process monitoring applications, where knowing whether a sample resembles a certain reference type can point to a specific process problem. This feature makes the method of the present invention useful as part of a process control feedback loop.

The method of the present invention also comprises the step of comparing the value for each of the normalized textural parameters for the first, or unknown, sample to the value for the corresponding normalized textural parameter for the second, or goal, sample to determine whether the first sample has a texture similar to the texture of the second sample. By "similar", it is meant that the values for NSD, NDD and NS for the first sample fall within a certain predetermined range, where the corresponding values for the second, or goal, sample are within this predetermined range. In the carpet embodiment of the present invention, if the values of NSD, NDD and NS for the first, or unknown, sample fall within this predetermined range, then the first sample is characterized as having the same texture as the second, or goal, sample. More specifically, in the carpet embodiment of the present invention, if the values of NSD, NDD and NS for the first, or unknown, sample fall within a specific predetermined range and the second, or goal, sample is a saxony-type carpet having a predetermined surface texture, which may be a tightly tailored surface texture, then the first sample is characterized as having the same surface texture as the second sample. Thus, if a carpet has normalized textural parameters which fall within the predetermined ranges as defined by the two versions of the carpet embodiment described below, it is a saxony-type carpet having a tightly tailored surface texture and a Visual Rating of either 3 or 4 on the Visual Rating Scale.

In one version of the carpet embodiment of the method of the present invention, the value for the normalized sum of the absolute difference (NSD) in contrast parameters is less than about 130, the value for the normalized absolute difference of the absolute difference (NDD) in contrast parameters is in the range of about 75 to 146, and the value for the normalized sum (NS) of the contrast parameters is in the range of about 95 to 140, where the second, or goal sample is a carpet having a tightly tailored surface texture as shown in FIG. 4. In another version of the carpet embodiment, NSD is less than about 130, NDD is greater than about 75, and NS is in the range of about 95 to 110, where the second, or goal sample is a saxony-type carpet having a tightly tailored surface texture as shown in FIG. 4.

In accordance with a further embodiment of the present invention, there is provided a saxony-type carpet having a tightly tailored surface texture and characterized by a set of normalized contrast parameters. Such a carpet is shown in FIG. 8. The carpet comprises multifilament yarn wherein the filaments of the yarn have substantially the same shrinkage values, and the ply-twist level of the yarn is below about 4.25 turns per inch (1.67 turns per centimeter). In one version of this embodiment of the present invention, the normalized contrast parameters meet the following conditions. The normalized sum of the absolute difference (NSD) in contrast parameters of the sample for a first and a second position in each of a first and a second direction of the sample is less than about 130, where the second position is rotated 180° from the first position, and the second stroke direction is reversed by 180° from the first stroke direction. The normalized absolute difference of the absolute difference (NDD) in contrast parameters for the first and second positions in each of the first and second stroke directions is in the range of about 75 to 146. Also, the normalized sum (NS) of the contrast parameters for the first and second positions in each of the first and second stroke directions is in the range of about 95 to 140, where the second, or goal sample is a carpet having a tightly tailored surface texture as shown in FIG. 4. It is preferable that the yarn has a twist level in the range of 3.0 to 4.2 turns per inch (1.18 to 1.65 turns per centimeter). It is further preferable that the yarn comprises substantially 100% crimped filaments. It is also preferable that the yarn, which may have a twist level in the range of 3.0 to 4.2 turns per inch (1.18 to 1.65 turns per centimeter) and which may comprise substantially 100% crimped filaments, may comprise either nylon 66 or nylon 6 yarn.

In another version of this further embodiment of the present invention, there is provided a saxony-type carpet having a tightly tailored surface texture and characterized by a set of normalized contrast parameters. Such a carpet is shown in FIG. 8. The carpet comprises multifilament yarn wherein the filaments of the yarn have substantially the same shrinkage values, and the ply-twist level of the yarn is below about 4.25 turns per inch (1.67 turns per centimeter). In this version, the normalized contrast parameters meet the following conditions. The normalized sum of the absolute difference (NSD) in contrast parameters of the sample for a first and a second position in each of a first and a second stroke direction of the sample is less than about 130, where the second position is rotated 180° from the first position, and the second stroke direction is reversed by 180° from the first stroke direction. The normalized absolute difference of the absolute difference (NDD) in contrast parameters for the first and second positions in each of the first and second stroke directions is greater than about 75. Also, the normalized sum (NS) of the contrast parameters for the first and second positions in each of the first and second stroke directions is in the range of about 95 to 110, where the second, or goal sample is a carpet having a tightly tailored surface texture as shown in FIG. 4. It is preferable that the yarn has a twist level in the range of 3.0 to 4.2 turns per inch (1.18 to 1.65 turns per centimeter). It is further preferable that the yarn comprises substantially 100% crimped filaments. It is also preferable that the yarn, which may have a twist level in the range of 3.0 to 4.2 turns per inch (1.18 to 1.65 turns per centimeter) and which may comprise substantially 100% crimped filaments, may comprise either nylon 66 or nylon 6 yarn.

In accordance with still another embodiment of the present invention, there is provided a saxony-type carpet having a tightly tailored surface texture and characterized by a set of normalized contrast parameters. Such a carpet is shown in FIG. 8. The carpet comprises yarn wherein the ply-twist level of the yarn is below about 4.25 turns per inch (1.67 turns per centimeter). In one version of this embodiment of the present invention, the normalized contrast parameters meet the following conditions. The normalized sum of the absolute difference (NSD) in contrast parameters of the sample for a first and a second position of the sample in each of a first and a second direction of the sample is less than about 130, where the second position is rotated 180° from the first position, and the second stroke direction is reversed by 180° from the first stroke direction. The normalized absolute difference of the absolute difference (NDD) in contrast parameters for the first and second positions in each of the first and second stroke directions is in the range of about 75 to 146. Also, the normalized sum (NS) of the contrast parameters for the first and second positions in each of the first and second stroke directions is in the range of about 95 to 140, where the second, or goal sample is a carpet having a tightly tailored surface texture as shown in FIG. 4. It is preferable that the yarn has a twist level in the range of 3.0 to 4.2 turns per inch (1.18 to 1.65 turns per centimeter). It is also preferable that the yarn, which may have a twist level in the range of 3.0 to 4.2 turns per inch (1.18 to 1.65 turns per centimeter), may comprise either nylon 66 or nylon 6 yarn.

In another version of this embodiment of the present invention, there is provided a saxony-type carpet having a tightly tailored surface texture and characterized by a set of normalized contrast parameters. Such a carpet is shown in FIG. 8. The carpet comprises yarn having a ply-twist level of below about 4.25 turns per inch (1.67 turns per inch). In this other version, the normalized contrast parameters meet the following conditions. The normalized sum of the absolute difference (NSD) in contrast parameters of the sample for a first and a second position in each of a first and a second stroke direction of the sample is less than about 130, where the second position is rotated 180° from the first position, and the second stroke direction is reversed by 180° from the first stroke direction. The normalized absolute difference of the absolute difference (NDD) in contrast parameters for the first and second positions in each of the first and second stroke directions is greater than about 75. Also, the normalized sum (NS) of the contrast parameters for the first and second positions in each of the first and second stroke directions is in the range of about 95 to 110, where the second, or goal sample is a carpet having a tightly tailored surface texture as shown in FIG. 4. It is preferable that the yarn has a twist level in the range of 3.0 to 4.2 turns per inch (1.18 to 1.65 turns per centimeter). It is also preferable that the yarn, which may have a twist level in the range of 3.0 to 4.2 turns per inch (1.18 to 1.65 turns per centimeter), may comprise either nylon 66 or nylon 6 yarn.

The process as described herein and the carpet produced by this process will be further clarified by the following examples, which are intended to be purely exemplary of the invention. The following testing methods were used in Examples 1–4 below.

Measurement of Ply-Twist Level in Yarns

The ply-twist level of the yarns, in turns per inch (which may be converted to turns per centimeter), was measured on a Precision Twist Tester, manufactured by Alfred Suter Co., Inc., of Orangeburg, N.Y. A convenient length of the yarn was mounted into the twist counter and tensioned with approximately 0.1 grams per denier (gpd) force. The twist counting mechanism of the instrument was set to zero, and the rotatable clamp was turned until all the twist of the individual singles yarns in the ply-yarn were removed. The removal of the twist was verified by moving a stylus between the singles yarns. The ply-twist level in turns per inch was then computed by the following formula:

$$\text{Twist Level (turns/inch)} = \frac{\text{Turns to remove twist}}{\text{Initial Length of plied} - \text{yarn}} \quad (7)$$

Measurement of Ply-Twist Level in Tufts (Turns Per Inch)

The ply-twist level of individual tufts, in turns per inch (which may be converted to turns per centimeter), may be measured by taking a photomicrograph of the tufts from a side perspective at a known magnification. The distance between the singles yarns along the longitudinal axis of the ply-twisted yarns is measured on the photomicrograph. The ends of the tuft, where the ply-twist level may be distorted by the carpet backing or unraveling, should be avoided. The ply-twist level is then computed by the following formula:

$$\text{Twist Level (turns/inch)} = \frac{\text{Magnification of Photomicrograph}}{(\text{Measured Distance Between Singles Yarns}) \times (\text{Number of Singles Yarns in Plied} - \text{Yarn})} \quad (8)$$

Measurements should be made on a minimum of 10 tufts to obtain a representative value of the ply-twist level.

Measurement of Yarn Bulk

Yarn bulk was measured using a method known in the art as described in U.S. Pat. No. 4,295,252. The yarn bulk levels are reported herein as % bulk crimp elongation (% BCE) as described in the '252 Patent. The bulk measurements were made at 11 m./min. for 1.5 minutes using a sample length of 16.5 m. The tensioning weight used was 0.1 gram./denier (0.11 g./dtex). The pressure of the air in the heating chamber was 1.27 mm. of water, and the temperature of the heating air was 170°±3° C.

Measurement of Modification Ratio

The modification ratio is defined and measured in Bankar et al., U.S. Pat. No. 4,492,731, the disclosure of which is incorporated herein by reference.

EXAMPLE 1

In this Example, a quantity of carpet yarn was heat-treated by the process as described above with respect to FIG. 7, and carpets were manufactured from these heat-treated yarns.

The singles yarn used was commercially available 1480 denier high bulk (35% BCE) nylon 66 bulked continuous filament (BCF), sold by Du Pont as 1480/P943, "Fiber for Stainmaster$^{cm}$ Carpets".

The cabling operation was done on a direct cabling machine commonly used in the trade to prepare such yarns. The ply-twist level of the input yarn was 4.03 turns per inch (1.59 turns per centimeter), and the ply-twist level of the carpet was 4.47 turns per inch (1.76 turns per centimeter).

The yarn was processed by passing it through the steam tube shown schematically in FIG. 7, which added moisture to and increased the temperature of the yarn. The yarn was then fed into a stuffer box, Model No. MF, commercially available from Superba Co. of Mulhouse, France. The yarn was then fed through a standard commercial configuration Superba ® carpet yarn heat-setting machine fitted with a pre-bulker, heat-setting chamber, dryer and wind-ups, commercially available from Superba Co., Model No. TVP.

Twelve (12) yarn ends were run through the process, described above, at a yarn speed of 144 m./min., which was about 35 kg./hour yarn throughput.

The steam tube was mounted such that the yarn outlet end was about 2.5 cm. from the stuffer box entrance. The apparatus was 0.47 m. long with an inner diameter of 0.64 cm. The residence time of the volume of yarn in the steam tube was about 0.2 seconds, and the yarn was heated to a temperature of about 50° C. and saturated.

The stuffer box was run at standard operating conditions which included a gate setting of 5 on the arbitrary scale provided on the device.

Belt speed through the pre-bulker, heat-setting chamber and dryer was 6 m./min. The residence time in the heat-setting chamber was about 60 seconds. The heat-setting chamber was run at 2.15 Bar, at 132° C.

Cut pile carpet samples were made using standard carpet ⅛ th inch gauge tufting equipment. The carpets had a face fiber weight of 1.22 kg./sq. m. and a 1.43 cm. finished pile height. After tufting, carpets were dyed on a Kuster continuous dyeing apparatus. After dyeing, the carpets were latexed by standard procedures and twice sheared on standard carpet shearing equipment. The carpet samples were evaluated on the Visual Rating Scale. The results are shown in Table 1 below of Example 2.

EXAMPLE 2

In this comparative Example, carpet yarn was treated in the same manner as described in Example 1, except that the yarn was not preheated and moisturized prior to entering the stuffer box.

The singles yarn used was 1420 denier high bulk (34% BCE) nylon 66 bulked continuous filament (BCF) test yarn which is similar to the yarn used in Example 1. In this Example, the ply-twist level of the input yarn was 4.00 turns per inch (1.57 turns per centimeter), and the ply-twist level of the carpet was 4.80 turns per inch (1.89 turns per centimeter).

Carpet samples were made by the techniques used in Example 1 and evaluated by the Visual Rating Scale. The results are shown below in Table 1.

TABLE 1

| Example No. | Visual Rating | NSD | NDD | NS | Quality |
|---|---|---|---|---|---|
| 1 | 3.5 | 87 | 137 | 118 | Pass |
| 2 | 4.5 | 89 | 204 | 90 | Fail |

EXAMPLE 3

In this Example, a quantity of carpet yarn was heat-treated and evaluated in the same manner as described in Example 1, except for the differences specified below.

The singles yarn was commercially available 1410 denier medium bulk (21% BCE) nylon 66 bulked continuous filament (BCF), sold by Du Pont as 1410/696AS, "Fiber for Stainmaster$^{cm}$ Carpets".

The ply-twist level of the input yarn was 3.78 turns per inch (1.49 turns per centimeter), and the ply-twist level of the carpet was 4.57 turns per inch (1.80 turns per centimeter). Twelve (12) yarn ends were run through the process described above at a yarn speed of 152 m./min. This was about 35 kg./hour throughput.

The steam tube was mounted such that the yarn outlet end was about 2.5 cm. from the stuffer box entrance. The steam tube was 0.47 m. long with an inner diameter of 0.64 cm. The residence time of the volume of yarn in the steam tube was about 0.2 seconds, and the yarn was heated to a temperature of about 50° C. and saturated.

The stuffer box was run at standard operating conditions which included a gate setting of 5 on the arbitrary scale provided on the device.

Belt speed through the pre-bulk, heat-setting chamber and dryer was 6 m./min. The residence time in the heat-setting chamber was about 60 seconds. The heat-setting chamber was run at 2.15 Bar, at 132° C.

Carpet samples were made by the techniques described in Example 1 and evaluated on the Visual Rating Scale. The results are shown in Table 2 in Example 4 below.

EXAMPLE 4

In this comparative Example, carpet yarn was treated in the same manner as described in Example 3, except the yarn was not preheated and moisturized prior to entering the stuffer box.

The singles yarn used was commercially available 1410 denier medium bulk (21% BCE) nylon 66 bulked continuous filament (BCF), sold by Du Pont as 1410/696AS, "Fiber for Stainmaster$^{cm}$ Carpets" and was from the same supply of yarn used in Example 3. In this Example, the ply-twist level of the input yarn was 3.78 turns per inch (1.49 turns per centimeter), and the ply-twist level of the carpet was 4.47 turns inch (1.76 turns per centimeter).

Carpet samples were made by the techniques described in Example 1 and evaluated on the Visual Rating Scale. The results are shown in Table 2 below.

TABLE 2

| Example No. | Visual Rating | NSD | NDD | NS | Quality |
|---|---|---|---|---|---|
| 3 | 5 | 60 | 148 | 129 | Fail |
| 4 | 5.5 | 78 | 181 | 111 | Fail |

The method for analyzing the texture of saxony-type carpet will be exemplified by the following Example 5, which is intended to be purely exemplary of the invention.

EXAMPLE 5

The laboratory set-up used in this Example comprised a Digital Equipment Corporation Vaxstation II computer equipped with a frame grabber and processor, a Sony XC-77 CCD video camera and a MacBeth Spectra light box. The samples were positioned so that the axis of the tufts of the carpet was perpendicular to and the tufts faced the viewing direction of the camera and so that the axis of the tufts was at about a 65° angle to the illumination source in the light box. The camera area of view was 18.42 cm.×14.0 cm. with a Nikon 35 mm. lens set at f 5.6. By viewing the sample normally and by illuminating it obliquely, the perspective errors were minimized, and local contrast due to tuft pile lay was maximized.

The pile lay of the carpet was enhanced by stroking the carpet with a ruler in different directions and then viewing it from different sides. A sample of a saxony-type carpet having a tightly tailored surface texture as shown in FIG. 4 ($S_4$) and a sample of straight-set, saxony-type carpet of the prior art (SAX) were each tested at two different f-stop settings, which determined the amount of light entering the camera, and at the four different combinations of position and stroke direction, which maximized the difference in the normalized contrast parameters of the samples of carpet. The values for NSD and NDD were calculated for each sample at each of the two camera settings in a light level variation test. The results were tabulated in the table of FIG. 13. In column 3 of the table of FIG. 13, $D_2P_2$ corresponds to (2,2) in FIG. 9, $D_2P_4$ corresponds to (2,4) in FIG. 9, $D_4P_2$ corresponds to (4,2) in FIG. 9, and $D_4P_4$ corresponds to (4,4) in FIG. 9. The table of FIG. 13 shows the stability of the normalized contrast parameters over wide variations in light intensity (i.e., the light entering the camera was changed by a factor of two). This stability is due to the fact that NSD and NDD are normalized by the factor $(\bar{c}_1+\bar{c}_2+\bar{c}_3+\bar{c}_4)$. In this test, the total tuft width was nine pixels, so $\bar{c}_1$, $\bar{c}_2$, $\bar{c}_3$ and $\bar{c}_4$ were averaged over one full tuft period, and the contrast parameters were calculated at a base spatial period of 1.8 times the tuft period. Thus, the robustness of the method of the present invention by the light level variation test was established.

Then, one light setting, f 5.6, was chosen and four different measurements of $\bar{c}_1$ through $\bar{c}_4$ were made on eight different known samples, $S_1$-$S_6$, which correspond to the carpets as shown in FIGS. 1-6, respectively, on a non-textured, straight-set, saxony-type carpet of the prior art (SAX), having a rating on the Visual Rating Scale greater than 6, on a "poodle"-type or over-textured carpet of the prior art (POO) having a rating on the Visual Rating Scale than 1, and on a set of eleven unknown samples, $U_1$-$U_{11}$ as tabulated in FIG. 14. The designation "known" and "unknown" was indicative of the texture of the carpet surface. Unknown samples $U_1$-$U_6$ were made using a steam tube with the process as described above with respect to FIG. 7, and unknown samples $U_7$-$U_{11}$ were samples of carpets of the prior art.

Specifically, sample $U_1$ was made as described in Example 3 above. Sample $U_2$ was made under the same conditions as sample $U_1$, except that the stuffer box gate setting used in making sample $U_1$ was 5, whereas the gate setting used in making sample $U_2$ was 10. Samples $U_3$ and $U_4$ were made of nylon 6 by the method as described herein with respect to FIG. 7 using a steam tube under the same conditions as each other except that the gate setting used in making sample $U_3$ was 10, and the gate setting used in making sample $U_4$ was 5. Sample $U_5$ was made in accordance with the process as described in Example 1 above. Sample $U_6$ was made under the same conditions as sample $U_5$, except that the gate setting used in making sample $U_5$ was 5, and the gate setting used in making sample $U_6$ was 10. Sample $U_7$ was made of nylon 66 in accordance with the method as described in Example 4 which did not use steam in the stuffer box. Sample $U_8$ was made of the same fiber as that of sample $U_7$ in accordance with a different known method which used steam in the stuffer box. Sample $U_9$ was made of nylon 6 in accordance with a known method which did not use steam in the stuffer box. Sample $U_{10}$ was also made of nylon 6, but in accordance with a known method which used steam in the stuffer box. Sample $U_{11}$ was made of nylon 66, high-bulk yarn in accordance with the method as described in Example 2 above which did not use steam in the stuffer box.

Each sample was imaged in a first position and in a second position rotated apart 180° from the first position and in a first stroke direction and in a second stroke direction reversed by 180° from the first stroke direction for each position. The table of FIG. 14 shows the values of the individual contrast parameters for each sample, as well as the normalized parameters NDD, NSD and NS. As in the light level variation test described above with respect to FIG. 13, the total tuft width was nine pixels, so that $\bar{c}_1$ through $\bar{c}_4$, respectively, were averaged over one full tuft period, and the contrast parameters were calculated at a base spatial period of 1.8 times the tuft period. The next to last column in the table in FIG. 14 shows the Visual Rating on the Visual Rating Scale of each sample. The last column in the table in FIG. 14 shows whether the sample was a saxony-type carpet having a tightly tailored surface texture on the basis of the Visual Rating Scale, a "PASS" indicating that a saxony-type carpet had a tightly tailored surface texture, and a "FAIL" indicated it did not. From this characterization on the basis of the Visual Rating Scale, a carpet was found to be a saxony-type carpet having a tightly tailored surface texture if the following conditions were met:

(NDD>75 AND<146) AND (NSD<130) AND
  (NS>95 AND<140)

OR (NDD>75) AND (NSD<130) AND (NS>95
  AND<110)

The two conditions set forth above predicted accurately the tightly tailored nature of the surface texture of all nineteen samples shown in FIG. 14.

The table as shown in FIG. 15 shows the results of a reproducibility test performed on a straight-set, saxony-type carpet of the prior art (SAX in the table of FIG. 14) to check the integrity of the measurement method of the present invention. In this test, a sample of SAX was imaged four different instances, in each case the sample being relocated in sample holder 14 as shown in FIG. 10, without being precise about the placement of the sample. The value for NSD for each of the four locations of the sample was calculated. The sample was tested at the four different combinations of position and stroke direction which maximized the difference in the normalized contrast parameters of the carpet. The camera was set at a constant f stop 5.6 for each image. As in the above tests, the total tuft width was nine pixels, so that $\bar{c}_1$ through $\bar{c}_4$, respectively, were averaged over one full tuft period, and the contrast parameters were calculated at a base spatial period of 1.8 times the tuft period. As can be seen from the table in FIG. 15, the values for NSD were stable, despite the varying locations of the sample within the sample holder. The results of the reproducibility test of FIG. 15 and of the light level variation test of FIG. 13 indicate that the normalized parameters are accurate measures of contrast.

Additional advantages and modifications will readily occur to those skilled in the art. The invention in its broader aspects is therefore, not limited to the specific details, representative apparatus and illustrative examples shown and described. Accordingly, departures may be made from such details without departing from the spirit or scope of the general inventive concept as defined by the appended claims and their equivalents.

We claim:

1. A method for analyzing the texture of a surface, comprising the steps of:
   (a) preparing a first sample of the surface;
   (b) generating at least one image of the first sample;
   (c) generating at least one normalized co-occurrence matrix from each image for a predetermined orientation and a predetermined spatial period;
   (d) calculating at least one textural parameter from each normalized co-occurrence matrix;
   (e) constructing a set of normalized textural parameters from the at least one textural parameter, wherein the normalized textural parameters are related to the physical properties of the surface;
   (f) calculating a value for each of the normalized textural parameters;
   (g) repeating steps (a)–(f) for a second sample; and
   (h) comparing the value for each of the normalized textural parameters for the first sample to the value for the corresponding normalized textural parameter for the second sample to determine whether the first sample has a texture similar to the texture of the second sample.

2. The method as claimed in claim 1, wherein the preparing step for the first and second samples includes preparing a sample of a carpet.

3. The method as claimed in claim 2, wherein the preparing step for the second sample includes preparing a sample of a textured, saxony-type carpet.

4. The method as claimed in claim 3, wherein the preparing step for the second sample includes preparing a sample of a textured, saxony-type carpet having a tightly tailored surface texture.

5. The method as claimed in claim 4, wherein the preparing step includes the sub-step of establishing the axis of the tufts of the sample.

6. The method as claimed in claim 5, wherein the preparing step further includes the sub-steps of:
   (i) stroking the carpet in a plurality of predetermined stroke directions, and
   (ii) positioning the carpet in a plurality of predetermined positions.

7. The method as claimed in claim 6, wherein the stroking sub-step includes the further sub-steps of:
   (A) stroking the sample in a first direction along the axis of the tufts, and
   (B) stroking the sample in a second direction reversed by 180° from the first direction along the axis of the tufts.

8. The method as claimed in claim 7, wherein the positioning sub-step includes the further sub-steps of:
   (C) orienting the sample to a first position so that the axis of the tufts is perpendicular to and the tufts face the viewing direction of a camera used to generate the image of the surface of the sample and so that the axis of the tufts is at an oblique angle to a light illumination source used to illuminate the sample after step (A),
   (D) rotating the sample by 180° to a second position so that the axis of the tufts remains perpendicular to and the tufts face the viewing direction of the camera and so that the axis of the tufts is at an oblique angle to the light illumination source after step (C),
   (E) orienting the sample to the second position so that the axis of the tufts is perpendicular to and the tufts face the viewing direction of the camera and so that the axis of the tufts is at an oblique angle to the light illumination source after step (B), and
   (F) rotating the sample by 180° to the first position so that the axis of the tufts remains perpendicular to and the tufts face the viewing direction of the camera and so that the axis of the tufts is at an oblique angle to the light illumination source after step (E).

9. The method as claimed in claim 8, wherein the oblique angle is about 65°.

10. The method as claimed in claim 8, wherein the generating step includes the sub-steps of:
    (I) generating a first image of the sample after step (C),
    (II) generating a second image of the sample after step (D),
    (III) generating a third image of the sample after step (E), and
    (IV) generating a fourth image of the sample after step (F).

11. The method as claimed in claim 10, wherein the step of calculating at least one textural parameter comprises calculating a contrast parameter for each of the first through fourth images, respectively.

12. The method as claimed in claim 11, wherein the step of calculating at least one textural parameter comprises the sub-steps of:
    (i) calculating the textural parameters for each integral increment of the spatial period range, and
    (ii) averaging the textural parameters over all the integral increments of the range of the spatial period.

13. The method as claimed in claim 12, wherein the spatial period is an integral value and is in the range of $1.8n \pm n/2$, where n is the spatial period of a predetermined tuft of the carpet.

14. The method as claimed in claim 13, wherein the step of calculating a value for each of the normalized textural parameters comprises the sub-steps of:
    (i) calculating a normalized sum of the absolute difference in contrast parameters for the first position and the second position in each of the first and the second stroke directions of the sample, where the second position is rotated 180° from the first position and the second stroke direction is reversed by 180° from the first stroke direction,
    (ii) calculating a normalized absolute difference of the absolute difference in contrast parameters for the first and second positions in each of the first and second stroke directions, and
    (iii) calculating a normalized sum of the contrast parameters for the first and second positions in each of the first and second stroke directions.

15. The method as claimed in claim 14, wherein:
    (A) the normalized sum of the absolute difference is less than about 130,
    (B) the normalized absolute difference of the absolute difference is in the range of about 75 to 146, and (C) the normalized sum of the contrast parameters is in the range of about 95 to 140.

16. The method as claimed in claim 14, wherein:
(A) the normalized sum of the absolute difference is less than about 130,
(B) the normalized absolute difference of the absolute difference is greater than about 75, and
(C) the normalized sum of the contrast parameters is in the range of about 95 to 110.

17. A saxony-type carpet having a tightly tailored surface texture and characterized by a set of normalized contrast parameters, the carpet comprising multifilament yarn wherein the filaments have substantially the same shrinkage values, the ply-twist level of the yarn is below about 1.67 turns per centimeter and wherein the normalized contrast parameters meet the following conditions:
(a) the normalized sum of the absolute difference in contrast parameters for a first and a second position in each of a first and a second stroke direction of a sample is less than about 130, where the second position is rotated 180° from the first position and the second stroke direction is reversed by 180° from the first stroke direction;
(b) the normalized absolute difference of the absolute difference in contrast parameters for the first and second positions in each of the first and second stroke directions is in the range of about 75 to 146; and
(c) the normalized sum of the contrast parameters for the first and second positions in each of the first and second stroke directions is in the range of about 95 to 140, where a goal sample comprises a saxony-type carpet having a tightly tailored surface texture.

18. The saxony-type carpet as claimed in claim 17, wherein the ply-twist level of the yarn is in the range of about 1.18 to 1.65 turns per centimeter.

19. The saxony-type carpet as claimed in claim 18, wherein the multifilament yarn comprises substantially 100% crimped filaments.

20. The saxony-type carpet as claimed in one of claims 17-19, wherein the yarn is nylon 66 yarn.

21. The saxony-type carpet as claimed in one of claims 17-19, wherein the yarn is nylon 6 yarn.

22. A saxony-type carpet having a tightly tailored surface texture and characterized by a set of normalized contrast parameters, the carpet comprising multifilament yarn comprising filaments having substantially the same shrinkage values, the ply-twist level of the yarn is below about 1.67 turns per centimeter and wherein the normalized contrast parameters meet the following conditions:
(a) the normalized sum of the absolute difference in contrast parameters between a first and a second position in each of a first and a second stroke direction of a sample is less than about 130, where the second position is rotated 180° from the first position and the second stroke direction is reversed by 180° from the first stroke direction;
(b) the normalized absolute difference of the absolute difference in contrast parameters for the first and second positions in each of the first and second stroke directions is greater than about 75; and
(c) the normalized sum of the contrast parameters for the first and second positions in each of the first and the second stroke directions is in the range of about 95 to 110, where a goal sample comprises a saxony-type carpet having a tightly tailored surface texture.

23. The saxony-type carpet as claimed in claim 22, wherein the ply-twist level of the yarn is in the range of about 1.18 to 1.65 turns per centimeter.

24. The saxony-type carpet as claimed in claim 23, wherein the multifilament yarn comprises substantially 100% crimped filaments.

25. The saxony-type carpet as claimed in one of claims 22-24, wherein the yarn is nylon 66 yarn.

26. The saxony-type carpet as claimed in one of claims 22-24, wherein the yarn is nylon 6 yarn.

* * * * *